(12) United States Patent
Sloan et al.

(10) Patent No.: US 10,494,602 B1
(45) Date of Patent: Dec. 3, 2019

(54) FUNCTIONAL ASTROCYTES AND CORTICAL NEURONS FROM INDUCED PLURIPOTENT STEM CELLS AND METHODS OF USE THEREOF

(71) Applicant: The Board of Trustees of the Leland Stanford Junior University, Stanford, CA (US)

(72) Inventors: Steven Sloan, Palo Alto, CA (US); Anca M. Pasca, Palo Alto, CA (US); Ben A. Barres, Palo Alto, CA (US); Sergiu P. Pasca, Palo Alto, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 529 days.

(21) Appl. No.: 15/158,408

(22) Filed: May 18, 2016

Related U.S. Application Data

(60) Provisional application No. 62/163,870, filed on May 19, 2015.

(51) Int. Cl.
*C12N 5/0793* (2010.01)
*G01N 33/50* (2006.01)

(52) U.S. Cl.
CPC ....... *C12N 5/0619* (2013.01); *G01N 33/5058* (2013.01); *C12N 2501/11* (2013.01); *C12N 2501/115* (2013.01); *C12N 2501/13* (2013.01); *C12N 2506/45* (2013.01)

(58) Field of Classification Search
CPC .................................................. C12N 5/0619
See application file for complete search history.

(56) References Cited

PUBLICATIONS

Schwindt et al. (2009, An Acad Bras Cienc, vol. 81(3), pp. 443-452) (Year: 2009).*
Gupta et al. (2012, Br. J. Clin. Pharmacol., vol. 75(4), pp. 907-918) (Year: 2012).*
Yuan et al. (2011, PLoS One, vol. 6(3), pp. 1-16) (Year: 2011).*
Oliveira et al. (2013, Cytomerty Part A, vol. 83A, pp. 76-89) (Year: 2013).*
Kim et al. (2010, Stem Cell Rev and Rep, vol. 6, pp. 270-281) (Year: 2010).*
Chen et al. (2014, Nature Communications, vol. 5, pp. 1-18) (Year: 2014).*
Mariani et al. (2012, PNAS, vol. 109(31), pp. 12770-12775 + Supplemental Data pp. 1-8) (Year: 2012).*
Royborn et al. (2013, Cell Repots, vol. 4, pp. 1035-1048). (Year: 2013).*
Takahashi et al. "Induction of Pluripotent Stem Cells from Adult Human Fibroblasts by Defined Factors" Cell, Nov. 30, 2007, pp. 131, 861-872, Elsevier Inc., Amsterdam, Netherlands.
Park et al. "Reprogramming of human somatic cells to pluripotency with defined factors", Jan. 10, 2008, Nature, pp. 141-146, vol. 451, Nature Publishing Group, London, United Kingdom.
Yu et al., "Induced Pluripotent Stem Cell Lines Derived from Human Somatic Cells" Science, Dec. 21, 2007, pp. 917-1920, vol. 318:1, Science/AAAS, Washington, DC.
Kim et al., "Generation of Human Induced Pluripotent Stem Cells by Direct Delivery of Reprogramming Proteins", Cell Stem Cell, Jun. 5, 2009, pp. 472-476, 4(6), NIH Public Access.
Soldner et al., "Parkinson's Disease Patient-Derived Induced Pluripotent Stem Cells Free of Viral Reprogramming Factors", Cell, Mar. 6, 2009, Mar. 6, 2009, pp. 964-977, 136, Elsevier Inc., Amsterdam, Netherlands.
Huangfu et al., Induction of pluripotent stem cells from primary human fibroblasts with only Oct4 and Sox2, Nov. 2008, Nature Biotechnology, pp. 1269-1275, vol. 26, No. 11, Nature Biotechnology, New York, NY.
Li et al., "Generation of Rat and Human Induced Pluripotent Stem Cells by Combining Genetic Reprogramming and Chemical Inhibitors", Cell Stem Cell, Jan. 9, 2009, pp. 16-19, Elsevier Inc., Amsterdam, Netherlands.
Mormone et al., 'Footprint-Free' Human Induced Pluripotent Stem Cell-Derived Astrocytes for In Vivo Cell-Based Therapy, Stem Cells and Development, 2014, pp. 2626-2636, vol. 23, No. 21, Mary Ann Liebert, Inc., New Rochelle, NY.
Yuan et al., "Human induced pluripotent stem cell-derived neural stem cells survive, migrate, differentiate, and improve neurologic function in a rat model of middle cerebral artery occlusion", Stem Cell Research and Therapy, 2013, pp. 1-10, 4:73; BioMed Central, London, United Kingdom.

* cited by examiner

*Primary Examiner* — Thaian N Ton
*Assistant Examiner* — David A Montanari
(74) *Attorney, Agent, or Firm* — Pamela J. Sherwood; Bozicevic, Field & Francis LLP

(57) ABSTRACT

Human pluripotent stem cells are differentiated in vitro into human cortical spheroids (hCS), which contain astrocytes, as well as cortical progenitors and neurons for use in analysis, screening programs, and the like.

11 Claims, 12 Drawing Sheets
(12 of 12 Drawing Sheet(s) Filed in Color)
Specification includes a Sequence Listing.

FIGURE 2A  FIGURE 2B  FIGURE 2C  FIGURE 2D  FIGURE 2E  FIGURE 2G
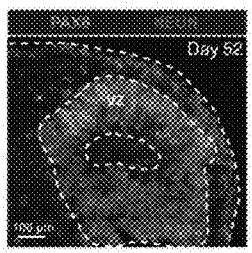 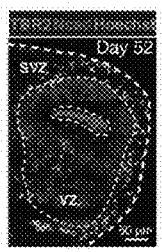 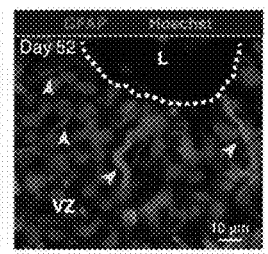 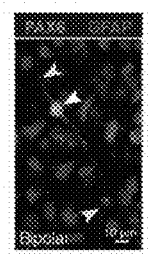 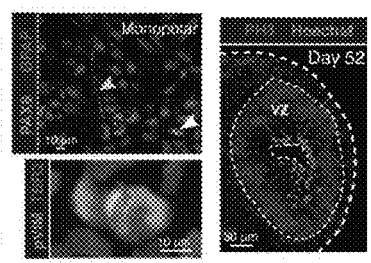
FIGURE 2H
FIGURE 2F
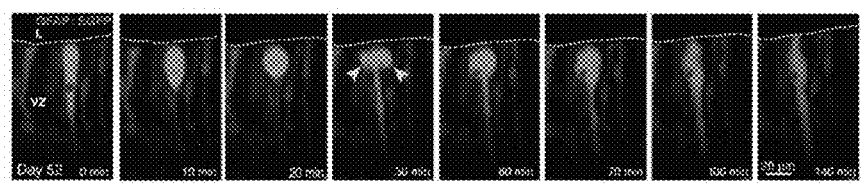 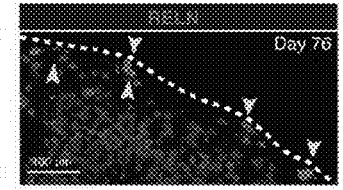
FIGURE 2J  FIGURE 2K  FIGURE 2L  FIGURE 2I
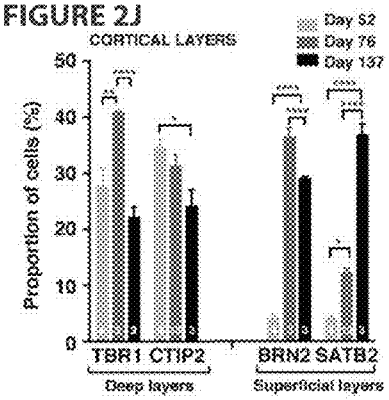 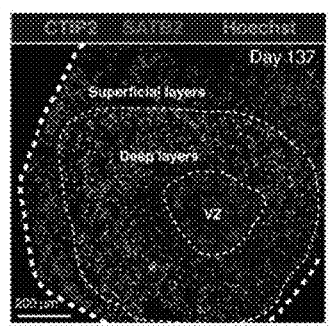 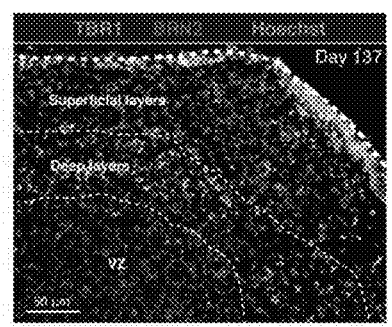
FIGURE 2O  FIGURE 2P
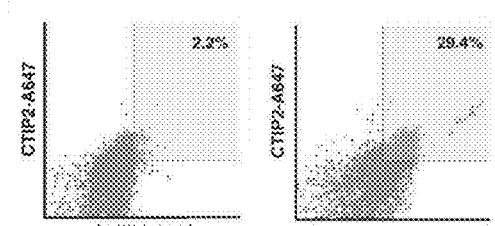 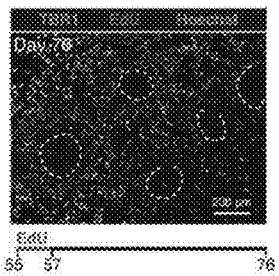 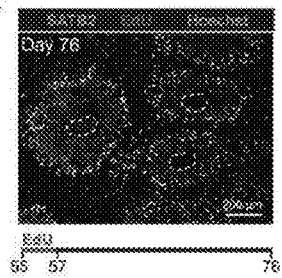
FIGURE 2M  FIGURE 2N FIGURE 3A
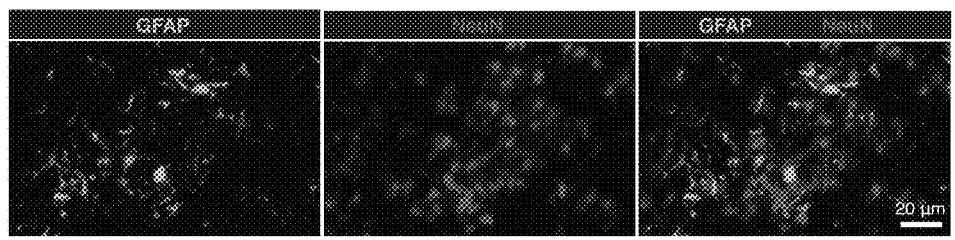
FIGURE 3B
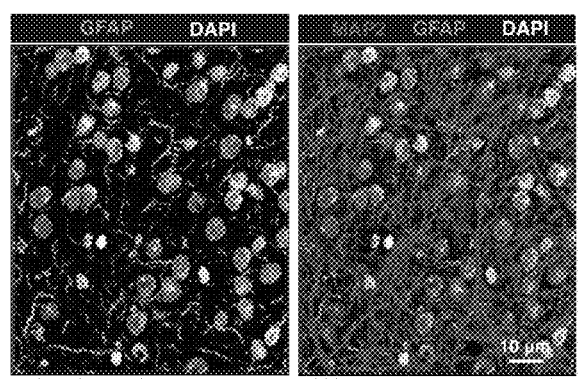
FIGURE 3C
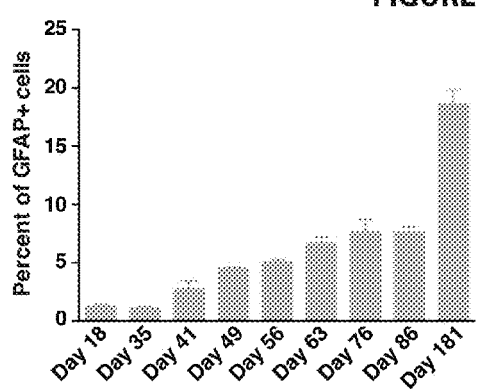
FIGURE 3D
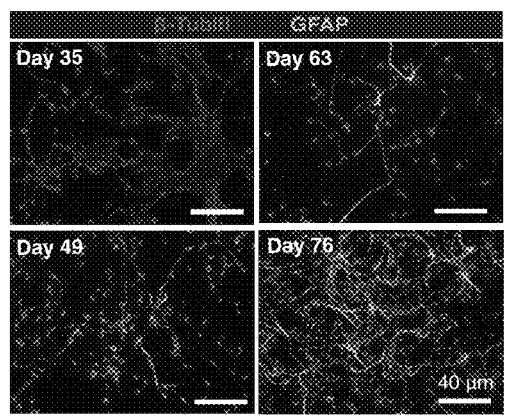
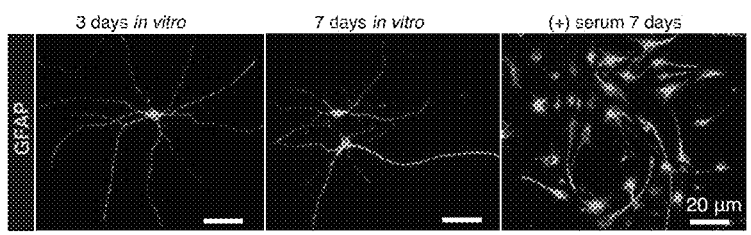
FIGURE 3E
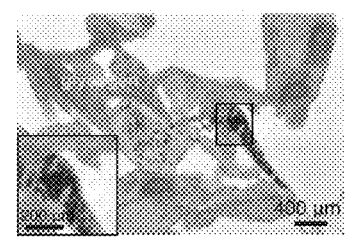
FIGURE 3F

FIGURE 5A
FIGURE 5B
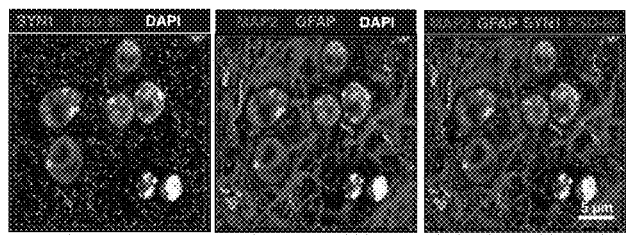
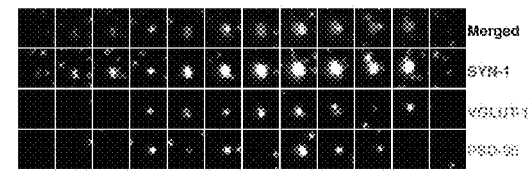
FIGURE 5C D-APS & NBQX  FIGURE 5D TTX  FIGURE 5E
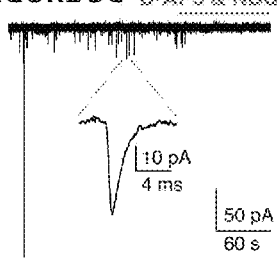
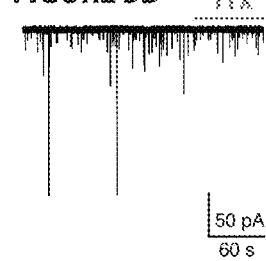
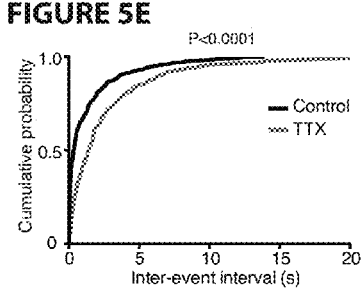
FIGURE 5G ACSF    Kynurenic
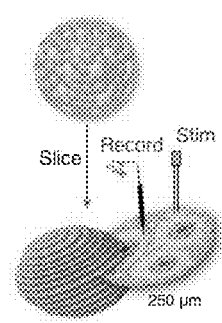
FIGURE 5I
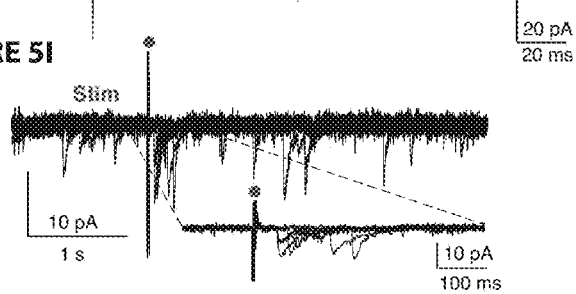
FIGURE 5F
FIGURE 5H
Biocytin-filled neuron
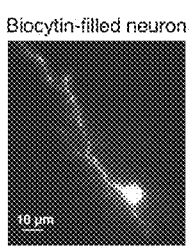
FIGURE 5J
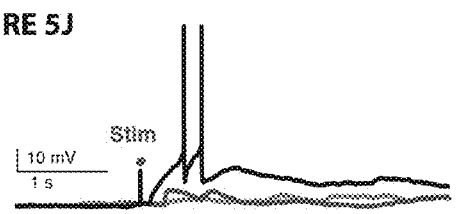

FIGURE 9A

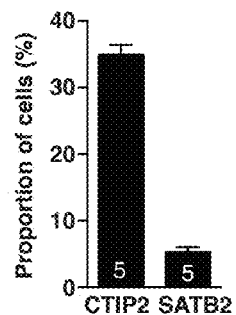
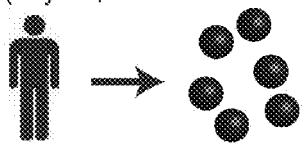

Variability across cortical spheroids (hCS)
Multiple spheroids differentiated
in parallel from one hiPSC line
(day 40, two cortical markers)

FIGURE 9B

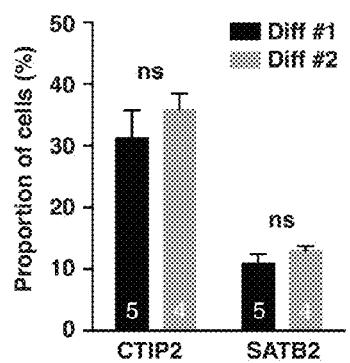
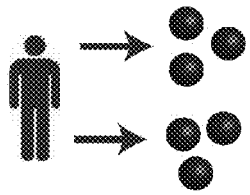

Variability across differentiations
Same hiPSC line differentiated in two
independent differentiation experiments
(day 76, two cortical layer markers)

FIGURE 9C

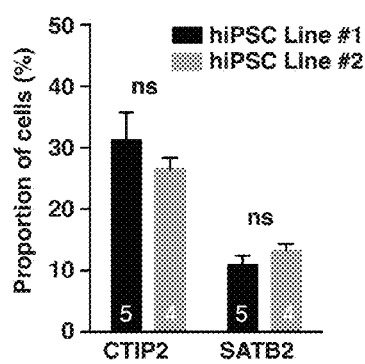
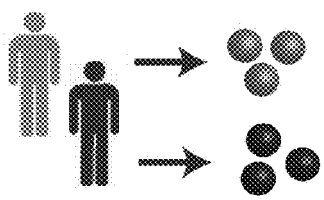

Variability across iPSC lines
Two iPSC lines from two different individuals
differentiated independently
(day 76, two cortical layer markers)

FIGURE 10A
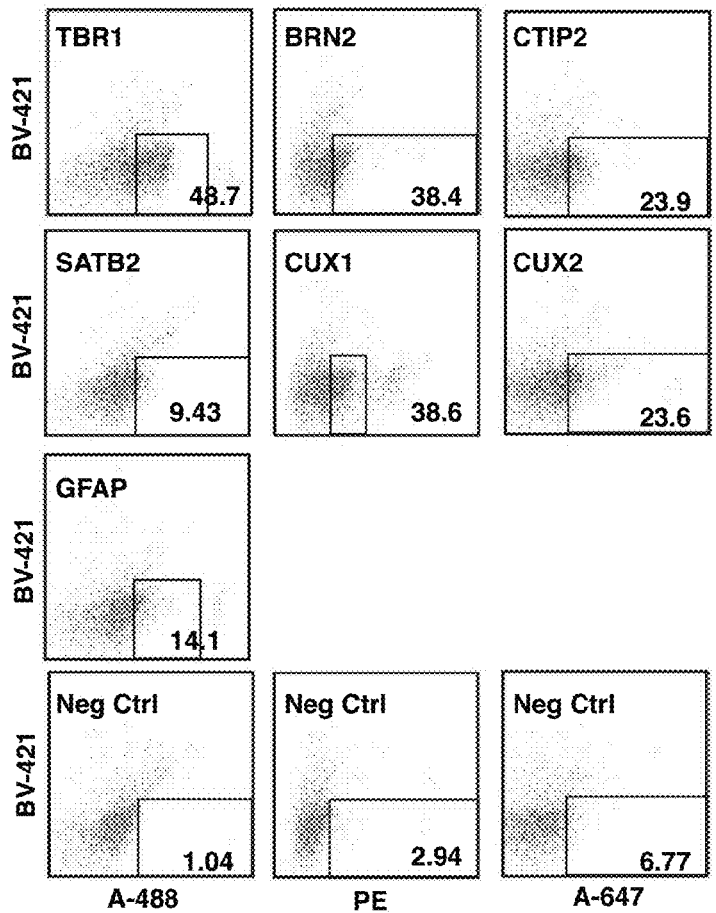
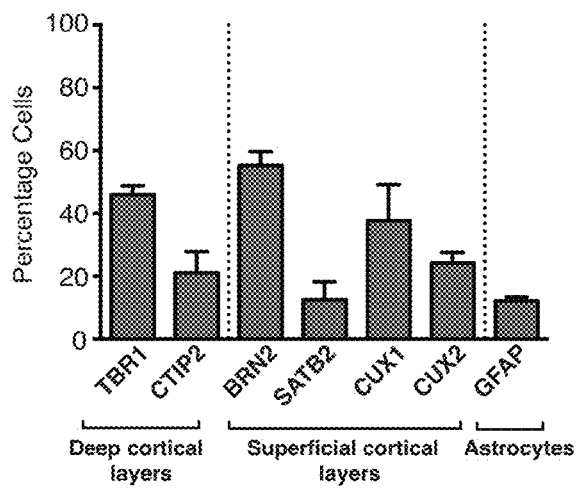
FIGURE 10B

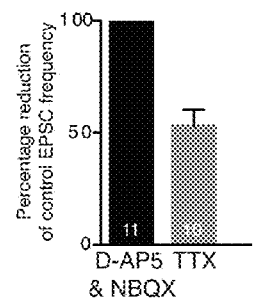
FIGURE 12A
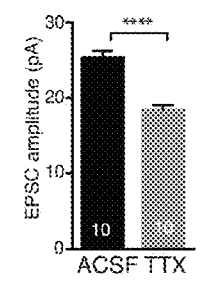
FIGURE 12B
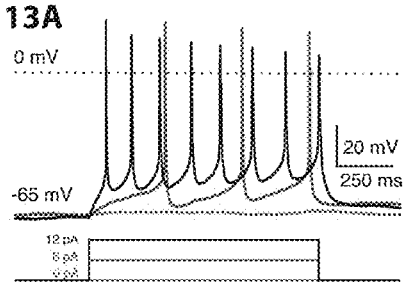
FIGURE 13A
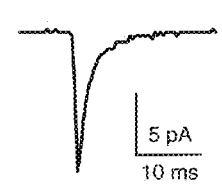
FIGURE 13B
FIGURE 13C
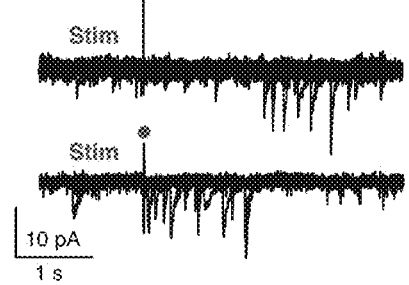
FIGURE 13D
FIGURE 13E
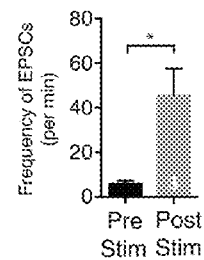
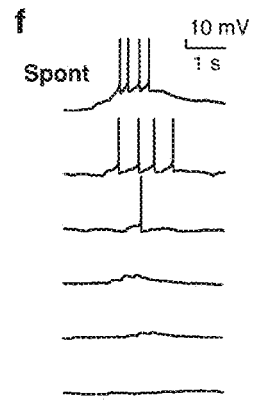
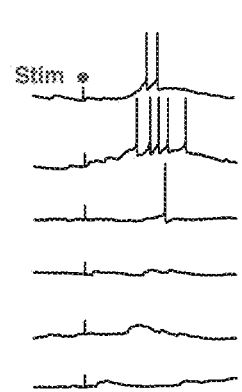

SEQUENCE LISTING

<160> NUMBER OF SEQ ID NOS: 8

<210> SEQ ID NO 1
<211> LENGTH: 21
<212> TYPE: DNA
<213> ORGANISM: Artificial Sequence
<220> FEATURE:
<223> OTHER INFORMATION: Synthetic nucleotide

<400> SEQUENCE: 1
gaacgggaag cttgtcatca a                                              21

<210> SEQ ID NO 2
<211> LENGTH: 20
<212> TYPE: DNA
<213> ORGANISM: Artificial sequence
<220> FEATURE:
<223> OTHER INFORMATION: Synthetic nucleotide

<400> SEQUENCE: 2
atcgccccac ttgattttgg                                                20

<210> SEQ ID NO 3
<211> LENGTH: 20
<212> TYPE: DNA
<213> ORGANISM: Artificial sequence
<220> FEATURE:
<223> OTHER INFORMATION: Synthetic nucleotide

<400> SEQUENCE: 3
gagaaccgga tcaccattcc                                                20

<210> SEQ ID NO 4
<211> LENGTH: 20
<212> TYPE: DNA
<213> ORGANISM: Artificial sequence
<220> FEATURE:
<223> OTHER INFORMATION: Synthetic nucleotide

<400> SEQUENCE: 4
cccagtctgg agcaacctac                                                20

<210> SEQ ID NO 5
<211> LENGTH: 20
<212> TYPE: DNA
<213> ORGANISM: Artificial sequence
<220> FEATURE:
<223> OTHER INFORMATION: Synthetic nucleotide

<400> SEQUENCE: 5
gttacctcgt ccgagtggtg                                                20

<210> SEQ ID NO 6
<211> LENGTH: 20
<212> TYPE: DNA
<213> ORGANISM: Artificial sequence
<220> FEATURE:
<223> OTHER INFORMATION: Synthetic nucleotide

<400> SEQUENCE: 6
ttggttctcc cgtagagggt                                                20

<210> SEQ ID NO 7
<211> LENGTH: 20
<212> TYPE: DNA
<213> ORGANISM: Artificial sequence

```
<220> FEATURE:
<223> OTHER INFORMATION: Synthetic nucleotide

<400> SEQUENCE: 7
ctccgggaga aattgcagga                                               20

<210> SEQ ID NO 8
<211> LENGTH: 20
<212> TYPE: DNA
<213> ORGANISM: Artificial sequence
<220> FEATURE:
<223> OTHER INFORMATION: Synthetic nucleotide

<400> SEQUENCE: 8
ttcaaggtca agacgtgcca                                               20
```

FUNCTIONAL ASTROCYTES AND CORTICAL NEURONS FROM INDUCED PLURIPOTENT STEM CELLS AND METHODS OF USE THEREOF

FEDERALLY SPONSORED RESEARCH AND DEVELOPMENT

This invention was made with Government support under contracts MH099555, MH100900, and MH106261 awarded by the National Institutes of Health. The Government has certain rights in the invention.

BACKGROUND OF THE INVENTION

Progress in understanding the intricate development of the human nervous system and elucidating the mechanisms of mental disorders in patients has been greatly limited by restricted access to functional human brain tissue. While studies in rodents have provided important insights into the fundamental principles of neural development, we know little about the cellular processes responsible for the massive expansion of the cerebral cortex in primates, nor many of its human specific features. In recent years, a paradigm shift has been achieved in the field with the introduction of cellular reprogramming—a process during which terminally differentiated somatic cells can be converted into pluripotent stem cells, named human induced pluripotent stem cells (hiPSC). These hiPSCs can be generated from any individual and, importantly, can be directed to differentiate in vitro into all germ layer derivatives, including neural cells.

While the methods and efficiency of generating hiPSCs have been significantly improved and standardized across laboratories, the methods for deriving specific neuronal cell types and glia remain challenging. Over the past decade, improvements in neural specification and differentiation protocols of pluripotent stem cells in monolayer have led to the generation of a variety of cell types. Nonetheless, two-dimensional (2D) methods are unlikely to recapitulate the cytoarchitecture of the developing three-dimensional (3D) nervous system or the complexity and functionality of in vivo neural networks and circuits. Moreover, these methods are laborious and costly, have limited efficiency and give rise to relatively immature neurons.

Rodent and human in vitro corticogenesis often appears incomplete and because synaptogenesis requires the presence of glial cells, studying synaptic function in hiPSC-derived neurons requires co-culture with astrocytes. This is currently achieved by separately differentiating neurons and glia and subsequently co-culturing them, or by plating hiPSC-derived neurons on a monolayer of rodent astrocytes. These needs have spawned 3D approaches for generating organoid cultures containing mixed ectodermal derivatives. Although these methods recapitulate many aspects of corticogenesis and display a level of self-organization beyond what is possible in 2D cultures, there are several limitations including the need for: (1) controlled specification and generation of neural cell types; (2) cortical lamination and the generation of equal proportions of superficial and deep layer neurons; (3) generation of non-reactive astrocytes; (4) robust synaptogenesis and spontaneous synaptic activity; (5) organization of a functional neural network that can be perturbed and probed using intact preparations; and (6) reproducibility between hiPSC lines/clones and within and across differentiations.

Pharmaceutical drug discovery, a multi-billion dollar industry, involves the identification and validation of therapeutic targets, as well as the identification and optimization of lead compounds. The explosion in numbers of potential new targets and chemical entities resulting from genomics and combinatorial chemistry approaches over the past few years has placed enormous pressure on screening programs. The rewards for identification of a useful drug are enormous, but the percentages of hits from any screening program are generally very low. Desirable compound screening methods solve this problem by both allowing for a high throughput so that many individual compounds can be tested; and by providing biologically relevant information so that there is a good correlation between the information generated by the screening assay and the pharmaceutical effectiveness of the compound.

Some of the more important features for pharmaceutical effectiveness are specificity for the targeted cell or disease, a lack of toxicity at relevant dosages, and specific activity of the compound against its molecular target. The present invention addresses this issue.

Publications.

Methods to reprogram primate differentiated somatic cells to a pluripotent state include differentiated somatic cell nuclear transfer, differentiated somatic cell fusion with pluripotent stem cells and direct reprogramming to produce induced pluripotent stem cells (iPS cells) (Takahashi K, et al. (2007) Cell 131:861-872; Park I H, et al. (2008) Nature 451:141-146; Yu J, et al. (2007) Science 318:1917-1920; Kim D, et al. (2009) Cell Stem Cell 4:472-476; Soldner F, et al. (2009) Cell. 136:964-977; Huangfu D, et al. (2008) Nature Biotechnology 26:1269-1275; Li W, et al. (2009) Cell Stem Cell 4:16-19).

Foot-print free derivation of astrocytes is described by Mormone et al. (2014) Stem Cells and Development. Induction of neural cells from pluripotent cells is described by Yuan et al. (2013) Stem Cell Research and Therapy 4:73.

SUMMARY OF THE INVENTION

Compositions and methods are provided for in vitro generation of human cortical spheroids and cells comprised therein, including, for example neural progenitors, astrocytes and cortical neurons. A feature of the invention is the ability to generate these cells, including without limitation astrocytes, from patient samples, allowing disease-relevant generation and screening of the cells for therapeutic drugs and treatment regimens, where the methods utilize in vitro cell cultures or animal models derived therefrom for such purposes. The methods utilize induced human pluripotent stem cells (hiPSCs), which may be obtained from patient or carrier cell samples, e.g. adipocytes, fibroblasts, and the like. The hiPSCs are induced to develop a neural fate in vitro, and then differentiated into human cortical spheroids (hCS), which contain astrocytes, as well as cortical progenitors and neurons. The cell populations can be isolated from the hCS, or the intact hCS can be used as a model for interacting neural cell populations. The hCS and cells derived therefrom may be used for transplantation, for experimental evaluation, as a source of lineage and cell specific products, and the like. In some embodiments the cell cultures are feeder-free and xeno-free.

In some embodiments of the invention, populations of purified human cells from the cortical spheroids, e.g. astrocytes, cortical progenitors, cortical neurons, etc. are provided, including without limitation disease-relevant astrocytes, where the cells are differentiated from induced human pluripotent stem cells (hiPSCs). Astrocytes can be quiescent, or can be readily activated. In some embodiments a panel of such in vitro derived cells are provided, where the panel includes two or more genetically different cells. In some embodiments a panel of such cells are provided, where the cells can be subjected to a plurality of candidate agents, or a plurality of doses of a candidate agent. Candidate agents include small molecules, i.e. drugs, genetic constructs that increase or decrease expression of an RNA of interest, electrical changes, and the like. In some embodiments a panel refers to a system or method utilizing patient-specific cells from two or more distinct conditions, and may be three or more, four or more, five or more, six or more, seven or more genetically distinct conditions.

In some embodiments of the invention, methods are provided for determining the activity of a candidate agent on human cells from the cortical spheroids (hCS), e.g. astrocytes, cortical progenitors, neurons, etc., the method comprising contacting the candidate agent with one or a panel of purified cell populations, which may be quiescent or activated astrocytes differentiated from induced human pluripotent stem cells (hiPSCs). The cell populations optionally comprise at least one allele encoding a mutation associated or potentially with a neuropsychiatric disease; and determining the effect of the agent on morphologic, genetic or functional parameters, including without limitation gene expression profiling. Methods of analysis at the single cell level are of particular interest, e.g. atomic force microscopy, patch clamping, single cell gene expression, live calcium imaging, modulation of synaptogenesis, and the like.

The methods of the invention utilize the natural interactions between neural cells and progenitors to differentiate astrocytes. The astrocytes can be isolated in a quiescent state, or can be activated by, for example, serum or other factors as known in the art. In some embodiments, the differentiation from hiPSCs to astrocyte is performed in substantially serum-free medium. In some embodiments, the differentiation from hiPSCs to astrocyte is performed in medium substantially free of the astrocyte activating factors, including specifically retinoic acid, TNFα, CNTF, FGF1, LIF and interferons.

After differentiation in an hCS, individual cell types of interest, including without limitation to astrocytes, can be isolated for various purposes. The cells are harvested at an appropriate stage of development, which may be determined based on the expression of markers and phenotypic characteristics of the desired cell type. Cultures may be empirically tested by immunostaining for the presence of the markers of interest, by morphological determination, etc. The cells are optionally enriched before or after the positive selection step by drug selection, panning, density gradient centrifugation, etc. In another embodiment, a negative selection is performed, where the selection is based on expression of one or more of markers found on human ES cells, fibroblasts, neural cells, epithelial cells, and the like. Selection may utilize panning methods, magnetic particle selection, particle sorter selection, and the like.

Various somatic cells find use as a source of hiPSCs; of particular interest are adipose-derived stem cells, fibroblasts, and the like. The use of hiPSCs from individuals of varying genotypes, particularly genotypes potentially associated with neurologic and psychiatric disorders are of particular interest. The hiPSCs are dissociated and grown in suspension; then induced to a neural fate by inhibition of BMP and TGFβ pathways. The spheroids are then moved to neural medium in the presence of FGF2 and EGF. To promote differentiation, the spheroids are changed to medium comprising BDNF and NT3. After such culture, the spheres can be maintained for extended periods of time in neural medium in the absence of growth factors, e.g. for periods of 1, 2, 3, 4, 5, 6, 7, 8, 9, 10, 11, 12 months or longer. The number of astrocytes in the cultures are initially low for the first month, and increase in number after that, up to from about 5%, about 10%, about 15%, about 20%, about 25%, to about 30% or more of the cells in the spheres.

These and other objects, advantages, and features of the invention will become apparent to those persons skilled in the art upon reading the details of the subject methods and compositions as more fully described below.

BRIEF DESCRIPTION OF THE DRAWINGS

The invention is best understood from the following detailed description when read in conjunction with the accompanying drawings. The patent or application file contains at least one drawing executed in color. Copies of this patent or patent application publication with color drawing(s) will be provided by the Office upon request and payment of the necessary fee. It is emphasized that, according to common practice, the various features of the drawings are not to-scale. On the contrary, the dimensions of the various features are arbitrarily expanded or reduced for clarity. Included in the drawings are the following figures.

FIG. 1B Immunostaining for PAX6 and FOXG1 in dissociated neural cultures at day 18 in vitro. FIG. 1C Proportion of TUBB3 (133-tubulin), NEUN, and GFAP expressing cells at days 49-52 and day 76 in vitro. Quantification performed in dissociated cells for TUBB3 and GFAP, and in cryosections for NEUN (mean±s.e.m.; n=3-6 hCS; two-way ANOVA, F1,20=47.67, $P<0.0001$ for time point, Bonferroni multiple comparison tests: , $P<0.01$; **, $P<0.0001$). FIG. 1D Morphology and size of hCS at day 13, day 26 and day 61 in vitro. For size comparison at day 61, a dissected E12.5 mouse brain is shown. FIG. 1E Transcriptional analyses and mapping onto the developing and adult human brain (age: 4PCW to >60 years) of the hCS at day 52 and day 76 using the machine-learning algorithm CoNTExT (n=3 hiPSC lines per time-point from three subjects). FIG. 1F Rank-rank hypergeometric overlap (RRHO) between hCS at day 52 and 76 (n=3 hiPSC clones), and laminae in the developing human cortex. MG: marginal zone; $CP_o$: outer cortical plate, $CO_i$: inner cortical plate; SP: subplate; IZ: intermediate zone; SZ: subventricular zone; SG: subpial granular layer.

FIG. 2A-2P. Corticogenesis in the hCS. FIG. 2A Cryosection of a hCS at day 52 of differentiation in vitro demonstrating the presence of a ventricular-like zone (VZ). PAX6 progenitors are organized around a lumen, while neurons expressing NEUN are localized outside the VZ-like region. FIG. 2B Intermediate progenitors cells expressing TBR2 are present in a subventricular-like zone (SVZ) beyond the VZ; NCAD (in red) stains the luminal side of the VZ progenitors. (FIG. 2C, FIG. 2D, FIG. 2E, FIG. 2F) Radial glial cells expressing GFAP, PAX6 or TBR2 and pVim are present in proliferative zones and extend processes perpendicular to the lumen FIG. 2L. When plated in monolayer (FIG. 2D, FIG. 2E), GFAP+/PAX6+ cells have either one or two processes FIG. 2G Mitoses, visualized with an anti-PH3 antibody, are spatially restricted to the luminal side of the proliferative zones. FIG. 2H Live cell imaging showing interkinetic nuclear migration in a cell expressing EGFP under the human GFAP promoter. FIG. 2I Neurons expressing reelin (RELN) are positioned horizontally on the surface of the hCS. FIG. 2J Quantification in cryosections of the proportion of cells expressing layer-specific cortical markers at three time points of in vitro differentiation (n=3-13 spheres per condition from 4 iPSC lines derived from 4 individuals; two-way ANOVA, F(2, 48)=32.96, P<0.0001 for timepoint; Tukey's multiple comparison tests: *, P<0.05; , P<0.01; *P<0.001; ****, P<0.0001). FIG. 2K & FIG. 2L Organization of layer-specific neurons in cryosections from 137 day old hCS. FIG. 2M & FIG. 2N Flow cytometry of dissociated hCS at 76 days in vitro showing the minimal overlap between CTIP2 (Alexa Fluo 647) and SATB2 (<3%) (Alexa Fluo 488) and the colocalization in ~30% of the cells of TBR1 (Alexa Fluo 488) and CTIP2 (Alexa Fluo 647). Negative control gates shown in FIG. 8a. FIG. 2O & FIG. 2P Timeline for the generation of deep layer TBR1+ neurons and superficial layer SABT2+ neurons. Cultures were loaded with EdU for 48 hours at 55 days of differentiation and analyzed 3 weeks later. Immunostaining of cryosections shows that the majority of the SATB2+ neurons were generated in the last stage of differentiation. Almost no additional deep layer TBR1-expressing neurons were generated in the last 3 weeks of differentiation.

FIG. 3A-3F. Astrogenesis in cortical hCS. FIG. 3A hCS at 76 days of differentiation in vitro contain GFAP+ cell bodies and thin processes alongside NEUN+ cells. FIG. 3B Volume rendering by array tomography (AT) of the interior of a hCS (74×88×2.45 μm) revealing the co-mingling of MAP2 (red) staining of neuronal dendrites, and GFAP (cyan) staining of glial processes. DAPI staining for nuclei is rendered in white. FIG. 3C & FIG. 3D Developmental time course (3 weeks to 6 months in vitro) for the generation of GFAP+ cells. Quantification in dissociated hCS (ANOVA F(8, 19)=66.75, P<0.0001). FIG. 3E Astrocytes exhibit complex process-bearing morphology after several days in vitro in defined, serum-free media. After a one-week exposure to serum, hiPSC derived astrocytes adopt a polygonal and hypertrophic morphology suggestive of an 'activated' state. FIG. 3F Transmission electron micrograph of a hCS section. An astrocyte process is pseudo-colored in cyan; the inset shows granules (yellow arrows) within a hCS.

FIG. 4A Time course of live calcium imaging in neurons dissociated from a hCS and cultured in monolayer (Fura-2 imaging). Arrows indicate active cells. FIG. 4B Average $[Ca^{2+}]_i$ measurements in the neurons indicated in panel FIG. 4A (cell#1-3) demonstrating spontaneous activity. FIG. 4C & FIG. 4D A representative trace of whole-cell voltage-clamp $Na^+$ current and $K^+$ currents recorded in neurons from dissociated hCS cultured in monolayer for two weeks (n=28 cells from hCS differentiated from two hiPSC clones; 20 mV steps from −70 mV). TTX (1 μM) blocks $Na^+$ currents. FIG. 4E Representative trace of a whole-cell current-clamp recording in human neurons from dissociated hCS cultured in monolayer for two weeks (n=9 cells from hCS differentiated from two hiPSC clones). The trace shows action potential generation (red and black upper traces) in response to 20 pA current injections (lower traces).

FIG. 5A-5J. FIG. 5A The distribution of structural (MAP2, GFAP) and synaptic proteins (SYN-1, PSD-95) inside hCS visualized with AT (volume: 29×29×2.45 μm). FIG. 5B "Synaptogram" (70 nm sections) revealing a synapse inside a hCS. Twelve consecutive sections are represented in each row and different antibody stains for the same section are represented in each column. (FIG. 5C, FIG. 5D) Representative traces of spontaneous EPSCs recorded at −70 mV in neurons derived in hCS and cultured in monolayer for two weeks, testing the effect of 25 μM NBQX and 50 μM D-AP5 FIG. 5C or of TTX FIG. 5D. (Quantification in FIG. 12). FIG. 5E Cumulative distribution of EPSC interevent-interval in the absence or presence of TTX (P<0.0001, Kolmogorov-Smirnov test, n=10 cells). FIG. 5F Schematic illustrating slicing of hCS, electrophysiological recordings and stimulation. FIG. 5G Representative EPSC traces recorded before (black) and during (blue) application of kynurenic acid in an acute slice preparation. FIG. 5H Biocytin-filled neuron after recording. FIG. 5I Voltage clamp recordings showing EPSCs after electrical stimulation in an acute hCS slice preparation. Composite of seven overlaid sweeps from a neuron. Inset shows stimulus evoked EPSCs at higher temporal resolution. The electrical stimulation artifact is designated by a red dot. Other examples and quantification shown in FIG. 13D, FIG. 5J. FIG. 5J Current clamp recordings of action potentials (black trace), EPSPs (red trace) and failures (blue trace) evoked by electrical stimulation (red dot) of hCS slices. Another example shown in FIG. 13F.

FIG. 8A CTIP2 and SATB2. FIG. 8B TBR1. FIG. 8C CTIP2 and BRN2. FIG. 8D CTIP2, SATB2 and CUX2.

FIG. 9A-9C. Variability in the generation of hCS. FIG. 9A Proportion of neurons (mean±s.e.m.) expressing CTIP2 and SATB2 at day 40 of differentiation. Multiple spheroids differentiated at the same time from one hiPSC line. Standard deviation is 2.9% for CTIP2 and 1.5% for SATB2. FIG. 9B Proportion of neurons (mean±s.e.m.) expressing CTIP2 and SATB2 at day 76 of differentiation. The same hiPSC line was differentiated in two different experiments at two different times (multiple hCS per differentiation). Two-way ANOVA, F(1,14)=0.1940, P=0.66 for iPSC lines; multiple comparison test P>0.05. FIG. 9C Proportion of neurons (mean±s.e.m.) expressing CTIP2 and SATB2 at day 76 of differentiation. Two hiPSC lines derived from two individuals were differentiated at two different times (multiple hCS per differentiation). Two-way ANOVA, F(1,14)=1.257, P=0.28; multiple comparison test P>0.05.

FIG. 10A-10B. Flow cytometry analysis of hCS. FIG. 10A Example of scatter plots for each of the antibodies used (first three rows) and the secondary only control conditions (fourth row). The marker of interest is presented on the x axis and the threshold gate is based on the negative control samples (cells stained with secondary antibodies alone). The y-axis represents a "dump channel", a BV-421 fluorescent channel in which the cells were not stained with any fluorophores. Any positive signals on this BV-421 channel represent highly auto-fluorescent cells or false positives and were excluded from the actual positive gates. FIG. 10B Quantification of the proportion of cells expressing various markers at day 76 of in vitro differentiation as assessed by flow cytometry.

FIG. 12A-12B. Electrophysiology (monolayer hCS) FIG. 12A Pharmacology of synaptic currents in neurons derived in hCS and plated in monolayer (at −70 mV). The frequency of EPSCs was abolished by NBQX (25 µM) and D-AP5 (50 µM) (paired t-test, n=11 cells, P=0.001), and was significantly reduced by 1 µM TTX (Wilcoxon signed-rank test, n=10, P=0.002). FIG. 12B TTX significantly reduced the amplitude of the EPSCs (P<0.0001, paired t-test, versus ACSF, n=10 cells).

FIG. 13A-13E. Electrophysiology (slice recordings) FIG. 13A Representative trace of a whole-cell current-clamp recording in an acute hCS slice preparation. Current injections (6 or 12 pA steps from −65 mV) produce sustained action potential generation. FIG. 13B Representative averaged trace of 53 sEPSCs in an individual hCS neuron under control conditions. FIG. 13C EPSCs were blocked by bath application of kynurenic acid in sliced hCSs (t-test, n=6 cells; P=0.0008). FIG. 13D Examples of voltage clamp recordings in two different hCSs showing EPSCs after electrical stimulation in an acute hCS slice preparation. Electrical stimulation artifact is designated by a red dot. FIG. 13E EPSC frequency 1 s prior compared to 2 s after electrical stimulation (t-test, n=3 cells; P=0.02) FIG. 13F Left: Representative traces of spontaneous action potentials (black traces) and compound EPSPs (red traces). Right: Representative examples of stimulus-evoked action potentials (black traces) and compound EPSPs (red traces). Electrical stimulation artifact is designated by a red dot.

Figure 1A:
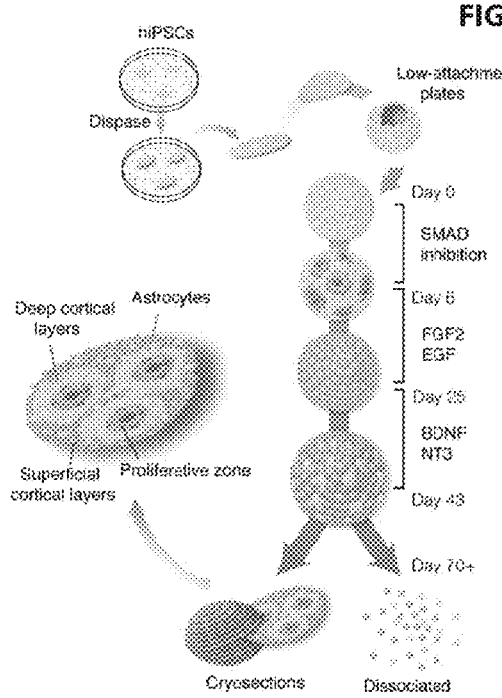
FIG. 1A-1F. Generation and characterization of the human cortical spheroids (hCS) FIG. 1A Scheme illustrating the main stages of the protocol for generating hCS from hiPSC. The hCS can either be dissociated for flow cytometry, monolayer culture, or can be fixed and sectioned for immunofluorescence experiments.
Figure 1B:
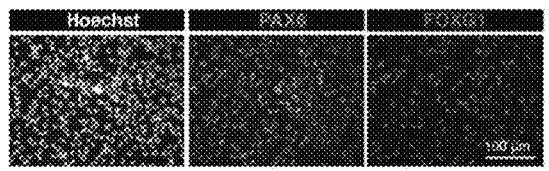

The invention is best understood from the following detailed description when read in conjunction with the accompanying drawings.

DETAILED DESCRIPTION OF THE INVENTION

Before the present compositions and methods are described, it is to be understood that this invention is not limited to particular compositions and methods described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits is included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

It must be noted that as used herein and in the appended claims, the singular forms "a", "an", and "the" include plural referents unless the context clearly dictates otherwise. Thus, for example, reference to "a reprogramming factor polypeptide" includes a plurality of such polypeptides, and reference to "the induced pluripotent stem cells" includes reference to one or more induced pluripotent stem cells and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Definitions

By "pluripotency" and pluripotent stem cells it is meant that such cells have the ability to differentiate into all types of cells in an organism. The term "induced pluripotent stem cell" encompasses pluripotent cells, that, like embryonic stem (ES) cells, can be cultured over a long period of time while maintaining the ability to differentiate into all types of cells in an organism, but that, unlike ES cells, are derived from differentiated somatic cells, that is, cells that had a narrower, more defined potential and that in the absence of experimental manipulation could not give rise to all types of cells in the organism. hiPSC have an human ES-like morphology, growing as flat colonies with large nucleo-cytoplasmic ratios, defined borders and prominent nuclei. In addition, hiPSC express several pluripotency markers known by one of ordinary skill in the art, including but not limited to alkaline phosphatase, SSEA3, SSEA4, Sox2, Oct3/4, Nanog, TRA160, TRA181, TDGF 1, Dnmt3b, FoxD3, GDF3, Cyp26a1, TERT, and zfp42. In addition, the hiPSC are capable of forming teratomas. In addition, they are capable of forming or contributing to ectoderm, mesoderm, or endoderm tissues in a living organism.

As used herein, "reprogramming factors" refers to one or more, i.e. a cocktail, of biologically active factors that act on a cell to alter transcription, thereby reprogramming a cell to multipotency or to pluripotency. Reprogramming factors may be provided to the cells, e.g. cells from an individual with a family history or genetic make-up of interest for heart disease such as fibroblasts, adipocytes, etc.; individually or as a single composition, that is, as a premixed composition, of reprogramming factors. The factors may be provided at the same molar ratio or at different molar ratios. The factors may be provided once or multiple times in the course of culturing the cells of the subject invention. In some embodiments the reprogramming factor is a transcription factor, including without limitation, Oct3/4, Sox2; Klf4; c-Myc; Nanog; and Lin-28.

Somatic cells are contacted with reprogramming factors, as defined above, in a combination and quantity sufficient to reprogram the cell to pluripotency. Reprogramming factors may be provided to the somatic cells individually or as a single composition, that is, as a premixed composition, of reprogramming factors. In some embodiments the reprogramming factors are provided as a plurality of coding sequences on a vector. The somatic cells may be fibroblasts, adipocytes, stromal cells, and the like, as known in the art. Somatic cells or hiPSC can be obtained from cell banks, from normal donors, from individuals having a neurologic or psychiatric disease of interest, etc.

Following induction of pluripotency, hiPSC are cultured according to any convenient method, e.g. on irradiated feeder cells and commercially available medium. The hiPSC can be dissociated from feeders by digesting with protease, e.g. dispase, preferably at a concentration and for a period of time sufficient to detach intact colonies of pluripotent stem cells from the layer of feeders.

Genes may be introduced into the somatic cells or the hiPSC derived therefrom for a variety of purposes, e.g. to replace genes having a loss of function mutation, provide marker genes, etc. Alternatively, vectors are introduced that express antisense mRNA or ribozymes, thereby blocking expression of an undesired gene. Other methods of gene therapy are the introduction of drug resistance genes to enable normal progenitor cells to have an advantage and be subject to selective pressure, for example the multiple drug resistance gene (MDR), or anti-apoptosis genes, such as bcl-2. Various techniques known in the art may be used to introduce nucleic acids into the target cells, e.g. electroporation, calcium precipitated DNA, fusion, transfection, lipofection, infection and the like, as discussed above. The particular manner in which the DNA is introduced is not critical to the practice of the invention.

The terms "astrocytic cell," "astrocyte," etc. encompass cells of the astrocyte lineage, i.e. glial progenitor cells, astrocyte precursor cells, and mature astocytes, which for the purposes of the present invention arise from a non-astrocytic cell by experimental manipulation. Astrocytes can be identified by markers specific for cells of the astrocyte lineage, e.g. GFAP, ALDH1L1, AQP4, EAAT1-2, etc. Markers of reactive astrocytes include S-100, VIM, LCN2, Fgfr3 and the like. Astrocytes may have characteristics of functional astrocytes, that is, they may have the capacity of promoting synaptogenesis in primary neuronal cultures; of accumulating glycogen granules in processes; of phagocytosing synapses; and the like. A "astrocyte precursor" is defined as a cell that is capable of giving rise to progeny that include astrocytes.

Astrocytes are the most numerous and diverse neuroglial cells in the CNS. An archetypal morphological feature of astrocytes is their expression of intermediate filaments, which form the cytoskeleton. The main types of astroglial intermediate filament proteins are glial fibrillary acidic protein (GFAP) and vimentin; expression of GFA, ALDH1L1 and/or AQP4P are commonly used as a specific marker for the identification of astrocytes.

The functions of astroglial cells are many: astrocytes create the brain environment, build up the micro-architecture of the brain parenchyma, integrate neural circuitry with local blood flow and metabolic support, maintain brain homeostasis, store and distribute energy substrates, control the development of neural cells, synaptogenesis and synaptic maintenance and provide for brain defense. As such, there is considerable interest in studying the effects of drugs and other therapeutic regimens on astrocytic cells.

In the mammalian brain the astroglial cells define the micro-architecture of the parenchyma by dividing the grey matter (through the process known as "tiling") into relatively independent structural units. The protoplasmic astrocytes occupy their own territory and create the micro-anatomical domains within the limits of their processes. Within the confines of these anatomical domains the membrane of the astrocyte covers synapses and neuronal membranes, as well as sends processes to plaster the wall of the neighboring blood vessel with their endfeet. The complex astrocyte-neurons-blood vessel is generally known as a neurovascular unit.

Astroglial cells can control extracellular homeostasis in the brain. By virtue of multiple molecular cascades, astrocytes control concentrations of ions, neurotransmitters and metabolites and regulate water movements. Glutamate is the major excitatory neurotransmitter in the brain of vertebrate, however when released in excess or for long-time, glutamate acts as a neurotoxin. Astrocytes remove the bulk of glutamate from the extracellular space by excitatory amino acid transporters (EAAT). Five types of EAATs are present in the human brain; the EAAT1 and EAAT2 are expressed almost exclusively in astrocytes, which utilize the energy saved in the form of transmembrane $Na^+$ gradient. Astroglial glutamate transport is crucial for neuronal glutamatergic transmission by operating the glutamate-glutamine shuttle. Glutamate, accumulated by astrocytes is enzymatically converted into glutamine by the astrocytic-specific glutamine synthetase. It is also of importance that astrocytes possess the enzyme pyruvate carboxylase, and thus act as a main source for de novo glutamate synthesis.

Astroglia regulate formation, maturation, maintenance, and stability of synapses, thus controlling the connectivity of neuronal circuits. Astrocytes secrete numerous factors required for synaptogenesis. Synaptic formation depends on cholesterol produced and secreted by astrocytes. Glial cells also affect synaptogenesis through signals influencing the expression of agrin and thrombin. Subsequently, astrocytes control maturation of synapses through several signaling systems, which affect the postsynaptic density, for example by controlling the density of postsynaptic receptors. Astroglia factors that affect synapse maturation include TNFα and activity-dependent neurotrophic factor (ADNF). Astrocytes may also limit the number of synapses.

Astrocytes and other glial cells can release a variety of transmitters into the extracellular space, including glutamate, ATP, GABA and D-serine. Mechanisms of release may include: diffusion through high-permeability channels (e.g. volume-activated Cl— channels, unpaired connexin "hemichannels" or P2X7 pore-forming purinoceptors; through transporters, e.g. by reversal of excitatory amino acid transporters or exchange via the cystine-glutamate antiporter or organic anion transporters.

Astrocytes are involved in all types of brain pathologies from acute lesions (trauma or stroke) to chronic neurodegenerative processes (such as Alexander's disease, Alzheimer's disease, Parkinson's disease, multiple sclerosis and many others) and psychiatric diseases. Pathologically relevant neuroglial processes include various programs of activation, which are essential for limiting the areas of damage, producing neuro-immune responses and for the post-insult remodeling and recovery of neural function.

Astroglial degeneration and atrophy in the early stages of various neurodegenerative disorders may be important for cognitive impairments.

In addition to various uses as in vitro cultured cells, the astrocytes may be tested in a suitable animal model. At one level, cells are assessed for their ability to survive and maintain their phenotype in vivo. Cell compositions are administered to immunodeficient animals (such as nude mice, or animals rendered immunodeficient chemically or by irradiation). Tissues are harvested after a period of regrowth, and assessed as to whether the administered cells or progeny thereof are still present, and may be phenotyped for response to a treatment of interest. Suitability can also be determined in an animal model by assessing the degree of recuperation that ensues from treatment with the differentiating cells of the invention.

Disease relevance. A number of pathologies are associated with astrocyte dysfunction, including Rett syndrome, fragile X mental retardation, Alexander's disease, and others. For example, amyotrophic lateral sclerosis (ALS) and/or frontotemporal dementia have implicated astrocyte dysfunction as potential drivers of these diseases. Rett syndrome, an X-linked neurodevelopmental disorder, is caused by the loss of the transcriptional repressor methyl-CpG-binding protein 2 (MeCP2.) Clinical features of the disease include autism, respiratory abnormalities, cognitive impairment, loss and regression of early developmental milestones, and a decrease in brain weight and volume. Evidence suggests that loss of MeCP2 function in astrocytes contributes to the developmental defects in neurons.

Fragile X syndrome, the most common cause of inherited intellectual disability, is caused by mutation of FMR1. Patients show cognitive impairment, autistic features, attention deficits, increased rates of epilepsy, and motor abnormalities. In humans, polyglutamine repeats in the FMR1 gene lead to loss of FMRP protein expression. Recent immunohistochemical studies demonstrate FMRP expression in developing astrocytes in vitro and possibly in vivo as well. Hippocampal neurons grown on FMR1-deficient astrocytes show abnormal dendritic morphology relative to those grown on wild-type astrocytes, and the intrinsic dendritic defects of FMR1-deficient neurons are significantly rescued when these cells are grown on a monolayer of wild type rather than FMR1-deficient astrocytes. The in vivo defects in dendritic spine development may be related to neuron-glia interactions during development.

Alexander's disease is due to a mutation in the astrocyte-specific protein GFAP. Clinically, it is characterized by macrocephaly, abnormal white matter, and developmental delay and is most commonly diagnosed in its infantile form, with onset before 2 years of age. The cardinal pathologic finding is cytoplasmic GFAP aggregates in astrocytes. Some individuals with GFAP point mutations have later onset or less severe symptoms than others.

The lysosomal storage disorder Niemann-Pick type C disease is caused by mutations in NPC1, which is localized primarily in astrocytic processes, and NP-C-deficient astrocytes showed some defects in cholesterol metabolism in culture.

Another broad category of neurological disorders that may involve astrocytes are the "RASopathies." These affect components of the Ras/MapK signaling pathway and include neurofibromatosis type-1 and Noonan, Leopard, CFC, and Costello syndromes. Clinical features across these disorders are variable, but frequently include varying degrees of neurocognitive delay. Studies in animal models suggest that signal dysregulation in these genetic diseases alters the timing of astrogliogenesis.

A neurocognitive disorder that may also involve timing of astrocyte development is Down syndrome (Trisomy 21). Recent work has shown that human neural progenitors from Down syndrome patients show a gliogenic shift and corresponding decrease in neurogenesis.

Mature and reactive astrocytes are involved in epileptogenesis via their effects on glutamate transport and release and their roles in buffering potassium and interstitial volume control. Astrocyte dysfunction in adult model systems can be involved in abnormal neuronal excitability, and inducing reactive astrocytosis can lead to the formation of epileptic foci in the hippocampus.

Autism spectrum disorders (ASDs) are neurodevelopmental disorders characterized by varying degrees of impaired social interaction and communication. Models of ASD emphasize the idea that abnormal synapse development underlies many features of the disease and postulate abnormalities in excitatory-inhibitory balance. A better understanding of astrocyte function or dysfunction in ASDs will shed light on pathogenesis and the development of new treatment strategies.

Changes in glial cell number or characteristics in the adult brains of patients with psychiatric disorders or in mouse models, including reductions in GFAP levels in prefrontal cortical and cortico-limbic areas in a rat model of depression and decreases in glial density in the amygdala in post-mortem samples of patients with depression. Recent evidence favors a developmental model of these diseases, particularly schizophrenia. Schizophrenia is defined by the presence of psychosis among other symptoms, and multiple lines of evidence support the idea that cortical "dysconnectivity," as a result of aberrant pre- or post-natal development, may be responsible for psychotic symptoms. Further attention to the roles of astrocytes is warranted, given their roles in postnatal synaptogenesis and myelination.

A recurrent theme in psychiatric diseases is the preferential dysfunction in specific brain regions, such as the prefrontal cortex, limbic system, and hippocampus. Many imaging studies have demonstrated volumetric changes in specific brain regions that could be related to glial cell loss or hypertrophy. Even more notable, noninvasive functional brain imaging techniques such as fMRI rely on measurements of neurovascular coupling (changes in blood flow to neurons), which occurs through astrocyte intermediates. Understanding the molecular and developmental basis for astrocyte regional heterogeneity may elucidate why and how specific brain regions or circuits are affected in different psychiatric diseases.

The terms "treatment", "treating", "treat" and the like are used herein to generally refer to obtaining a desired pharmacologic and/or physiologic effect. The effect may be prophylactic in terms of completely or partially preventing a disease or symptom thereof and/or may be therapeutic in terms of a partial or complete stabilization or cure for a disease and/or adverse effect attributable to the disease. "Treatment" as used herein covers any treatment of a disease in a mammal, particularly a human, and includes: (a) preventing the disease or symptom from occurring in a subject which may be predisposed to the disease or symptom but has not yet been diagnosed as having it; (b) inhibiting the disease symptom, i.e., arresting its development; or (c) relieving the disease symptom, i.e., causing regression of the disease or symptom.

The terms "individual," "subject," "host," and "patient," are used interchangeably herein and refer to any mammalian subject for whom diagnosis, treatment, or therapy is desired, particularly humans.

Methods of the Invention

Methods are provided for the obtention and use of in vitro cell cultures of human cortical spheroids and cells comprised therein, including, for example neural progenitors, astrocytes and cortical neurons, where the cells are differentiated from induced human pluripotent stem cells (hiPSC). In some embodiments the hiPSC are derived from somatic cells obtained from neurologically normal individuals. In other embodiments the hiPSC are derived from somatic cells obtained from an individual comprising at least one allele encoding a mutation associated with a neural disease, including without limitation the astrocyte associated diseases described above. In some embodiments a panel of such astrocytes are provided, where the panel includes two or more genetically different astrocytes. In some embodiments a panel of such astrocytes are provided, where the astrocytes are subjected to a plurality of candidate agents or other therapeutic intervention, or a plurality of doses of a candidate agent or other therapeutic intervention. Candidate agents include without limitation small molecules, i.e. drugs, genetic constructs that increase or decrease expression of an RNA of interest, electrical changes, and the like.

Methods are also provided for determining the activity of a candidate agent on a disease-relevant cell, the method comprising contacting the candidate agent with one or a panel of cells differentiated from human pluripotent stem cells, e.g. differentiated from ES cells or from hiPSC, where the pluripotent stem cells optionally comprise at least one allele encoding a mutation associated with a neural disease; and determining the effect of the agent on morphologic, genetic or functional parameters, including without limitation gene expression profiling.

Generation of human cortical spheroids (hCS) and cells comprised therein, including, for example neural progenitors, astrocytes and cortical neurons from somatic cells utilizes a multi-step process. Initially, hiPSC can be obtained from any convenient source, or can be generated from somatic cells using art-recognized methods. The hiPSC are dissociated from feeders and grown in suspension culture in the absence of FGF2, preferably when dissociated as intact colonies. In certain embodiments the culture are feeder layer free, e.g. when grown on vitronectin coated vessels. The culture may further be free on non-human components, i.e. xeno-free. Suspension growth optionally includes in the culture medium an effective dose of a selective Rho-associated kinase (ROCK) inhibitor for the initial period of culture, for up to about 6 hours, about 12 hours, about 18 hours, about 24 hours, about 36 hours, about 48 hours, (see, for example, Watanabe et al. (2007) Nature Biotechnology 25:681 686). Inhibitors useful for such purpose include, without limitation, Y-27632; Thiazovivin (Cell Res, 2013, 23(10):1187-200; Fasudil (HA-1077) HCl (J Clin Invest, 2014, 124(9):3757-66); GSK429286A (Proc Natl Acad Sci USA, 2014, 111(12):E1140-8); RKI-1447, AT13148; etc.

The suspension culture of hiPSC is then induced to a neural fate. This culture may be feeder-free. For neural induction, an effective dose of an inhibitor of BMP, and of TGFβ pathways is added to the medium, for a period at least about 2 days, at least about 3 days, at least about 4 days, at least about 5 days, and up to about 10 days, up to about 9 days, up to about 8 days, up to about 7 days, up to about 6 days, up to about 5 days. For example, dorsomorphin (DM) can be added at an effective dose of at least about 0.1 µM, at least about 1 µM, at least about 5 µM, at least about 10 µM, at least about 50 µM, up to about 100 µM concentration, which inhibits bone morphogenetic protein (BMP) type I receptors (ALK2, ALK3 and ALK6). Other useful BMP inhibitors include, without limitation, A 83-01; DMH-1; K 02288; ML 347; SB 505124; etc. SB-431542 can be added at an effective dose of at least about 0.1 µM, at least about 1 µM, at least about 5 µM, at least about 10 µM, at least about 50 µM, up to about 100 µM concentration, which inhibits TGFβ signaling but has no effect on BMP signaling. Other useful inhibitors of TGFβ include, without limitation, LDN-193189 (J Clin Invest, 2015, 125(2):796-808); Galunisertib (LY2157299) (Cancer Res, 2014, 74(21):5963-77); LY2109761 (Toxicology, 2014, 326C:9-17), SB525334 (Cell Signal, 2014, 26(12):3027-35); SD-208; EW-7197; Kartogenin; DMH1; LDN-212854; ML347; LDN-193189 HCl (Proc Natl Acad Sci USA, 2013, 110(52):E5039-48); SB505124, Pirfenidone (Histochem Cell Biol, 2014, 10.1007/s00418-014-1223-0); RepSox; K02288; Hesperetin; GW788388, LY364947, etc.

An effective dose of a wnt inhibitor may be included in the culture medium, for example at a concentration of from about 0.1 µM to about 100 µM, and may be from about 1 µM to about 25 µM, depending on the activity of the inhibitor that is selected. Exemplary inhibitors include, without limitation, XAV-939 selectively inhibits Wnt/β-catenin-mediated transcription through tankyrasel/2 inhibition with IC50 of 11 nM/4 nM in cell-free assays; ICG-001 antagonizes Wnt/β-catenin/TCF-mediated transcription and specifically binds to element-binding protein (CBP) with IC50 of 3 µM; IWR-1-endo is a Wnt pathway inhibitor with IC50 of 180 nM in L-cells expressing Wnt3A, induces Axin2 protein levels and promotes β-catenin phosphorylation by stabilizing Axin-scaffolded destruction complexes; Wnt-059 (C59) is a PORCN inhibitor for Wnt3A-mediated activation of a multimerized TCF-binding site driving luciferase with IC50 of 74 pM in HEK293 cells; LGK-974 is a potent and specific PORCN inhibitor, and inhibits Wnt signaling with IC50 of 0.4 nM in TM3 cells; KY02111 promotes differentiation of hPSCs to cardiomyocytes by inhibiting Wnt signaling, may act downstream of APC and GSK3β, IWP-2 is an inhibitor of Wnt processing and secretion with 1050 of 27 nM in a cell-free assay, selective blockage of Porcn-mediated Wnt palmitoylation, does not affect Wnt/β-catenin in general and displays no effect against Wnt-stimulated cellular responses; IWP-L6 is a highly potent Porcn inhibitor with EC50 of 0.5 nM; WIKI4 is a novel Tankyrase inhibitor with IC50 of 15 nM for TNKS2, and leads to inhibition of Wnt/beta-catenin signaling; FH535 is a Wnt/β-catenin signaling inhibitor and also a dual PPARγ and PPARδ antagonist.

After about 5 days, about 6 days, about 7 days, about 8 days, about 9 days, about 10 days in suspension culture, the floating spheroids are moved to neural media to differentiate neural progenitors. The media is supplemented with an effective dose of FGF2 and EGF. The growth factors can be provided at a concentration for each of at least about 0.5 ng/ml, at least about 1 ng/ml, at least about 5 ng/ml, at least about 10 ng/ml, at least about 20 ng/ml, up to about 500 ng/ml, up to about 250 ng/ml, up to about 100 ng/ml.

To promote differentiation of neural progenitors into neurons, after about 1 week, about 2 weeks, about 3 weeks, about 4 weeks after FGF2/EGF exposure the neural medium is changed to replace the FGF2 and EGF with an effective dose of BDNF and NT3. The growth factors can be provided at a concentration for each of at least about 0.5 ng/ml, at least about 1 ng/ml, at least about 5 ng/ml, at least about 10 ng/ml, at least about 20 ng/ml, up to about 500 ng/ml, up to about 250 ng/ml, up to about 100 ng/ml.

After about 4 weeks, about 5 weeks, about 6 weeks, about 7 weeks after FGF2/EGF exposure, the spheres can be maintained for extended periods of time in neural medium in the absence of growth factors, e.g. for periods of 1, 2, 3, 4, 5, 6, 7, 8, 9, 10, 11, 12 months or longer. The number of astrocytes in the cultures are initially low for the first month, and increase in number after that, up to from about 5%, about 10%, about 15%, about 20%, about 25%, to about 30% or more of the cells in the spheres. The astrocytes present in the hCS generally have a quiescent phenotype, i.e. low levels of expression markers of astrocyte activation, e.g. VIM and LCN2, etc.

Optionally the astrocyte population thus obtained can be activated by exposure to an effective dose of a suitable agent, including, for example, serum; and other growth factors, e.g. TNFα, CNTF, FGF1, interferons, and the like.

Populations of cells can be isolated from the cortical spheres by any convenient method, including flow cytometry, magnetic immunoselection, immunopanning, etc. Conveniently, GFAP is used as a positive selection marker for astrocytes. The cells thus isolated can be resuspended in an acceptable medium and maintained in culture, frozen, analyzed for parameters of interest; transplanted into a human or animal model; and the like.

Screening Assays

In screening assays for the small molecules, the effect of adding a candidate agent to cells in culture is tested with a panel of cells and cellular environments, where the cellular environment includes one or more of: electrical stimulation including alterations in ionicity, stimulation with a candidate agent of interest, contact with other cells including without limitation neurons and neural progenitors, and the like, and where panels of astrocytes may vary in genotype, in prior exposure to an environment of interest, in the dose of agent that is provided, etc. Usually at least one control is included, for example a negative control and a positive control. Culture of cells is typically performed in a sterile environment, for example, at 37° C. in an incubator containing a humidified 92-95% air/5-8% $CO_2$ atmosphere. Cell culture may be carried out in nutrient mixtures containing undefined biological fluids such as fetal calf serum, or media which is fully defined and serum free. The effect of the altering of the environment is assessed by monitoring multiple output parameters, including morphogical, functional and genetic changes.

In the screening assays for genetic agents, polynucleotides can be added to one or more of the cells in a panel in order to alter the genetic composition of the cell. The output parameters are monitored to determine whether there is a change in phenotype. In this way, genetic sequences are identified that encode or affect expression of proteins in pathways of interest. The results can be entered into a data processor to provide a screening results dataset. Algorithms are used for the comparison and analysis of screening results obtained under different conditions.

Methods of analysis at the single cell level are of particular interest, e.g. as described above: atomic force microscopy, single cell gene expression, single cell RNA sequencing, calcium imaging, flow cytometry and the like. Various parameters can be measured to determine the effect of a drug or treatment on the astrocytes.

Parameters are quantifiable components of cells, particularly components that can be accurately measured, desirably in a high throughput system. A parameter can also be any cell component or cell product including cell surface determinant, receptor, protein or conformational or posttranslational modification thereof, lipid, carbohydrate, organic or inorganic molecule, nucleic acid, e.g. mRNA, DNA, etc. or a portion derived from such a cell component or combinations thereof. While most parameters will provide a quantitative readout, in some instances a semi-quantitative or qualitative result will be acceptable. Readouts may include a single determined value, or may include mean, median value or the variance, etc. Variability is expected and a range of values for each of the set of test parameters will be obtained using standard statistical methods with a common statistical method used to provide single values.

Parameters of interest include detection of cytoplasmic, cell surface or secreted biomolecules, frequently biopolymers, e.g. polypeptides, polysaccharides, polynucleotides, lipids, etc. Cell surface and secreted molecules are a preferred parameter type as these mediate cell communication and cell effector responses and can be more readily assayed. In one embodiment, parameters include specific epitopes. Epitopes are frequently identified using specific monoclonal antibodies or receptor probes. In some cases the molecular entities comprising the epitope are from two or more substances and comprise a defined structure; examples include combinatorially determined epitopes associated with heterodimeric integrins. A parameter may be detection of a specifically modified protein or oligosaccharide. A parameter may be defined by a specific monoclonal antibody or a ligand or receptor binding determinant.

Candidate agents of interest are biologically active agents that encompass numerous chemical classes, primarily organic molecules, which may include organometallic molecules, inorganic molecules, genetic sequences, etc. An important aspect of the invention is to evaluate candidate drugs, select therapeutic antibodies and protein-based therapeutics, with preferred biological response functions. Candidate agents comprise functional groups necessary for structural interaction with proteins, particularly hydrogen bonding, and typically include at least an amine, carbonyl, hydroxyl or carboxyl group, frequently at least two of the functional chemical groups. The candidate agents often comprise cyclical carbon or heterocyclic structures and/or aromatic or polyaromatic structures substituted with one or more of the above functional groups. Candidate agents are also found among biomolecules, including peptides, polynucleotides, saccharides, fatty acids, steroids, purines, pyrimidines, derivatives, structural analogs or combinations thereof.

Included are pharmacologically active drugs, genetically active molecules, etc. Compounds of interest include chemotherapeutic agents, anti-inflammatory agents, hormones or hormone antagonists, ion channel modifiers, and neuroactive agents. Exemplary of pharmaceutical agents suitable for this invention are those described in, "The Pharmacological Basis of Therapeutics," Goodman and Gilman, McGraw-Hill, New York, N.Y., (1996), Ninth edition, under the sections: Drugs Acting at Synaptic and Neuroeffector Junctional Sites; Cardiovascular Drugs; Vitamins, Dermatology; and Toxicology, all incorporated herein by reference.

Test compounds include all of the classes of molecules described above, and may further comprise samples of unknown content. Of interest are complex mixtures of naturally occurring compounds derived from natural sources such as plants. While many samples will comprise compounds in solution, solid samples that can be dissolved in a suitable solvent may also be assayed. Samples of interest include environmental samples, e.g. ground water, sea water, mining waste, etc.; biological samples, e.g. lysates prepared from crops, tissue samples, etc.; manufacturing samples, e.g. time course during preparation of pharmaceuticals; as well as libraries of compounds prepared for analysis; and the like. Samples of interest include compounds being assessed for potential therapeutic value, i.e. drug candidates.

The term samples also includes the fluids described above to which additional components have been added, for example components that affect the ionic strength, pH, total protein concentration, etc. In addition, the samples may be treated to achieve at least partial fractionation or concentration. Biological samples may be stored if care is taken to reduce degradation of the compound, e.g. under nitrogen, frozen, or a combination thereof. The volume of sample used is sufficient to allow for measurable detection, usually from about 0.1:I to 1 ml of a biological sample is sufficient.

Compounds, including candidate agents, are obtained from a wide variety of sources including libraries of synthetic or natural compounds. For example, numerous means are available for random and directed synthesis of a wide variety of organic compounds, including biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

As used herein, the term "genetic agent" refers to polynucleotides and analogs thereof, which agents are tested in the screening assays of the invention by addition of the genetic agent to a cell. The introduction of the genetic agent results in an alteration of the total genetic composition of the cell. Genetic agents such as DNA can result in an experimentally introduced change in the genome of a cell, generally through the integration of the sequence into a chromosome. Genetic changes can also be transient, where the exogenous sequence is not integrated but is maintained as an episomal agents. Genetic agents, such as antisense oligonucleotides, can also affect the expression of proteins without changing the cell's genotype, by interfering with the transcription or translation of mRNA. The effect of a genetic agent is to increase or decrease expression of one or more gene products in the cell.

Introduction of an expression vector encoding a polypeptide can be used to express the encoded product in cells lacking the sequence, or to over-express the product. Various promoters can be used that are constitutive or subject to external regulation, where in the latter situation, one can turn on or off the transcription of a gene. These coding sequences may include full-length cDNA or genomic clones, fragments derived therefrom, or chimeras that combine a naturally occurring sequence with functional or structural domains of other coding sequences. Alternatively, the introduced sequence may encode an anti-sense sequence; be an antisense oligonucleotide; RNAi, encode a dominant negative mutation, or dominant or constitutively active mutations of native sequences; altered regulatory sequences, etc.

Antisense and RNAi oligonucleotides can be chemically synthesized by methods known in the art. Preferred oligonucleotides are chemically modified from the native phosphodiester structure, in order to increase their intracellular stability and binding affinity. A number of such modifications have been described in the literature, which alter the chemistry of the backbone, sugars or heterocyclic bases. Among useful changes in the backbone chemistry are phosphorothioates; phosphorodithioates, where both of the non-bridging oxygens are substituted with sulfur; phosphoroamidites; alkyl phosphotriesters and boranophosphates. Achiral phosphate derivatives include 3'-O'-5'-S-phosphorothioate, 3'-S-5'-O-phosphorothioate, 3'-CH2-5'-O-phosphonate and 3'-NH-5'-O-phosphoroamidate. Peptide nucleic acids replace the entire ribose phosphodiester backbone with a peptide linkage. Sugar modifications are also used to enhance stability and affinity, e.g. morpholino oligonucleotide analogs. The a-anomer of deoxyribose may be used, where the base is inverted with respect to the natural p-anomer. The 2'-OH of the ribose sugar may be altered to form 2'-O-methyl or 2'-O-allyl sugars, which provides resistance to degradation without comprising affinity.

Agents are screened for biological activity by adding the agent to at least one and usually a plurality of cells, in one or in a plurality of environmental conditions, e.g. following stimulation with a β-adrenergic agonist, following electric or mechanical stimulation, etc. The change in parameter readout in response to the agent is measured, desirably normalized, and the resulting screening results may then be evaluated by comparison to reference screening results, e.g. with cells having other mutations of interest, normal astrocytes, astrocytes derived from other family members, and the like. The reference screening results may include readouts in the presence and absence of different environmental changes, screening results obtained with other agents, which may or may not include known drugs, etc.

The agents are conveniently added in solution, or readily soluble form, to the medium of cells in culture. The agents may be added in a flow-through system, as a stream, intermittent or continuous, or alternatively, adding a bolus of the compound, singly or incrementally, to an otherwise static solution. In a flow-through system, two fluids are used, where one is a physiologically neutral solution, and the other is the same solution with the test compound added. The first fluid is passed over the cells, followed by the second. In a single solution method, a bolus of the test compound is added to the volume of medium surrounding the cells. The overall concentrations of the components of the culture medium should not change significantly with the addition of the bolus, or between the two solutions in a flow through method.

Preferred agent formulations do not include additional components, such as preservatives, that may have a significant effect on the overall formulation. Thus preferred formulations consist essentially of a biologically active compound and a physiologically acceptable carrier, e.g. water, ethanol, DMSO, etc. However, if a compound is liquid without a solvent, the formulation may consist essentially of the compound itself.

A plurality of assays may be run in parallel with different agent concentrations to obtain a differential response to the various concentrations. As known in the art, determining the effective concentration of an agent typically uses a range of concentrations resulting from 1:10, or other log scale, dilutions. The concentrations may be further refined with a second series of dilutions, if necessary. Typically, one of these concentrations serves as a negative control, i.e. at zero concentration or below the level of detection of the agent or at or below the concentration of agent that does not give a detectable change in the phenotype.

Various methods can be utilized for quantifying the presence of selected parameters, in addition to the functional parameters described above. For measuring the amount of a molecule that is present, a convenient method is to label a molecule with a detectable moiety, which may be fluorescent, luminescent, radioactive, enzymatically active, etc., particularly a molecule specific for binding to the parameter with high affinity fluorescent moieties are readily available for labeling virtually any biomolecule, structure, or cell type. Immunofluorescent moieties can be directed to bind not only to specific proteins but also specific conformations, cleavage products, or site modifications like phosphorylation. Individual peptides and proteins can be engineered to autofluoresce, e.g. by expressing them as green fluorescent protein chimeras inside cells (for a review see Jones et al. (1999) Trends Biotechnol. 17(12):477-81). Thus, antibodies can be genetically modified to provide a fluorescent dye as part of their structure Depending upon the label chosen, parameters may be measured using other than fluorescent labels, using such immunoassay techniques as radioimmunoassay (RIA) or enzyme linked immunosorbance assay (ELISA), homogeneous enzyme immunoassays, and related non-enzymatic techniques. These techniques utilize specific antibodies as reporter molecules, which are particularly useful due to their high degree of specificity for attaching to a single molecular target. U.S. Pat. No. 4,568,649 describes ligand detection systems, which employ scintillation counting. These techniques are particularly useful for protein or modified protein parameters or epitopes, or carbohydrate determinants. Cell readouts for proteins and other cell determinants can be obtained using fluorescent or otherwise tagged reporter molecules. Cell based ELISA or related non-enzymatic or fluorescence-based methods enable measurement of cell surface parameters and secreted parameters. Capture ELISA and related non-enzymatic methods usually employ two specific antibodies or reporter molecules and are useful for measuring parameters in solution. Flow cytometry methods are useful for measuring cell surface and intracellular parameters, as well as shape change and granularity and for analyses of beads used as antibody- or probe-linked reagents. Readouts from such assays may be the mean fluorescence associated with individual fluorescent antibody-detected cell surface molecules or cytokines, or the average fluorescence intensity, the median fluorescence intensity, the variance in fluorescence intensity, or some relationship among these.

Both single cell multiparameter and multicell multiparameter multiplex assays, where input cell types are identified and parameters are read by quantitative imaging and fluorescence and confocal microscopy are used in the art, see Confocal Microscopy Methods and Protocols (Methods in Molecular Biology Vol. 122.) Paddock, Ed., Humana Press, 1998. These methods are described in U.S. Pat. No. 5,989,833 issued Nov. 23, 1999.

The quantitation of nucleic acids, especially messenger RNAs, is also of interest as a parameter. These can be measured by hybridization techniques that depend on the sequence of nucleic acid nucleotides. Techniques include polymerase chain reaction methods as well as gene array techniques. See Current Protocols in Molecular Biology, Ausubel et al., eds, John Wiley & Sons, New York, N.Y., 2000; Freeman et al. (1999) Biotechniques 26(1):112-225; Kawamoto et al. (1999) Genome Res 9(12):1305-12, and Chen et al. (1998) Genomics 51(3):313-24, for examples.

The comparison of screening results obtained from a test compound, and a reference screening results(s) is accomplished by the use of suitable deduction protocols, AI systems, statistical comparisons, etc. Preferably, the screening results is compared with a database of reference screening results. A database of reference screening results can be compiled. These databases may include reference results from panels that include known agents or combinations of agents, as well as references from the analysis of cells treated under environmental conditions in which single or multiple environmental conditions or parameters are removed or specifically altered. Reference results may also be generated from panels containing cells with genetic constructs that selectively target or modulate specific cellular pathways.

The readout may be a mean, average, median or the variance or other statistically or mathematically derived value associated with the measurement. The parameter readout information may be further refined by direct comparison with the corresponding reference readout. The absolute values obtained for each parameter under identical conditions will display a variability that is inherent in live biological systems and also reflects individual cellular variability as well as the variability inherent between individuals.

For convenience, the systems of the subject invention may be provided in kits. The kits could include the cells to be used, which may be frozen, refrigerated or treated in some other manner to maintain viability, reagents for measuring the parameters, and software for preparing the screening results. The software will receive the results and perform analysis and can include reference data. The software can also normalize the results with the results from a control culture. The composition may optionally be packaged in a suitable container with written instructions for a desired purpose, such as screening methods, and the like.

For further elaboration of general techniques useful in the practice of this invention, the practitioner can refer to standard textbooks and reviews in cell biology, tissue culture, embryology, and neurobiology. With respect to tissue culture and embryonic stem cells, the reader may wish to refer to Teratocarcinomas and embryonic stem cells: A practical approach (E. J. Robertson, ed., IRL Press Ltd. 1987); Guide to Techniques in Mouse Development (P. M. Wasserman et al. eds., Academic Press 1993); Embryonic Stem Cell Differentiation in Vitro (M. V. Wiles, Meth. Enzymol. 225:900, 1993); Properties and uses of Embryonic Stem Cells: Prospects for Application to Human Biology and Gene Therapy (P. D. Rathjen et al., Reprod. Fertil. Dev. 10:31, 1998).

General methods in molecular and cellular biochemistry can be found in such standard textbooks as Molecular Cloning: A Laboratory Manual, 3rd Ed. (Sambrook et al., Harbor Laboratory Press 2001); Short Protocols in Molecular Biology, 4th Ed. (Ausubel et al. eds., John Wiley & Sons 1999); Protein Methods (Bollag et al., John Wiley & Sons 1996); Nonviral Vectors for Gene Therapy (Wagner et al. eds., Academic Press 1999); Viral Vectors (Kaplift & Loewy eds., Academic Press 1995); Immunology Methods Manual (I. Lefkovits ed., Academic Press 1997); and Cell and Tissue Culture: Laboratory Procedures in Biotechnology (Doyle & Griffiths, John Wiley & Sons 1998). Reagents, cloning vectors, and kits for genetic manipulation referred to in this disclosure are available from commercial vendors such as BioRad, Stratagene, Invitrogen, Sigma-Aldrich, and ClonTech.

Each publication cited in this specification is hereby incorporated by reference in its entirety for all purposes.

It is to be understood that this invention is not limited to the particular methodology, protocols, cell lines, animal species or genera, and reagents described, as such may vary. It is also to be understood that the terminology used herein is for the purpose of describing particular embodiments only, and is not intended to limit the scope of the present invention, which will be limited only by the appended claims.

As used herein the singular forms "a", "and", and "the" include plural referents unless the context clearly dictates otherwise. Thus, for example, reference to "a cell" includes a plurality of such cells and reference to "the culture" includes reference to one or more cultures and equivalents thereof known to those skilled in the art, and so forth. All technical and scientific terms used herein have the same meaning as commonly understood to one of ordinary skill in the art to which this invention belongs unless clearly indicated otherwise.

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

EXPERIMENTAL

Example 1

Generation of Functional Cortical Neurons and Astrocytes from Human Pluripotent Stem Cells in 3D Cultures The human cerebral cortex develops via an elaborate succession of cellular events, including neurogenesis and gliogenesis, which when disrupted can lead to neuropsychiatric disease. The ability to reprogram human somatic cells into pluripotent stem cells and differentiate these cells in vitro provides a unique opportunity to study normal and abnormal corticogenesis. Here, we present a simple and reproducible 3D culture approach for generating a laminated cerebral cortex-like structure, named human cortical spheroid (hCS), from human pluripotent cells. These hCS contain both deep and superficial layer cortical neurons and map transcriptionally to in vivo fetal development. The majority of neurons are electrophysiologically mature, display spontaneous activity, are surrounded by non-reactive astrocytes, and form functional synapses. Importantly, physiology experiments in acute slices of hCS demonstrate that cortical neurons participate in network activity and are capable of producing complex synaptic events associated with postsynaptic neuronal spike firing. Overall, these 3D cultures allow a detailed interrogation of human cortical development, function and disease, and represent a versatile platform for generating other neuronal and glial subtypes in vitro.

Here we report a simple method for generating pyramidal neurons from hiPSCs in a 3D cerebral cortex-like structure. These neural structures, named human cortical spheroids (hCS), are generated from intact hiPSC colonies that are cultured and minimally patterned in exclusively non-adherent conditions and in the absence of extracellular scaffolding. This approach to generate hCS overcomes many of the limitations of previous neural systems. Unlike multi-regional organoids, hCS generate only excitatory neurons of the dorsal telencephalon. Moreover, the internal cytoarchitecture is reminiscent of a laminated neocortex and can grow to include equal proportions of projecting neurons expressing deep and superficial layer cortical markers.

Transcriptional analysis using a validated computational framework and comparison to the developing and adult human brain reveals that hCS, measuring ~4 mm in diameter after 2 months in culture, resemble the mid-fetal prenatal brain (19-24 post-conception, PCW). Cortical neurons are accompanied by a network of non-reactive astrocytes and are synaptically connected. Importantly, hCS are amenable to acute slice physiology, which allows one to record and electrically stimulate neurons while preserving a relatively intact network. Lastly, this method is simple, scalable and reproducible between hiPSC lines, across and within differentiations. Therefore, hCS have the potential to unravel the mechanisms of neuropsychiatric disorders, identify biomarkers for early diagnosis and clinical stratification, and provide a platform for drug and teratologic agent screenings in vitro.

Results

Generation of hCS from hiPSC.

To generate suspended cellular aggregates of pluripotent cells, we used cultures of hiPSCs grown on a feeder layer (7 iPSC lines derived from 5 subjects). Rather than using single cell suspensions of pluripotent stem cells, we enzymatically detached intact hiPSC colonies from their inactivated feeders (FIG. 1a). To achieve this gentle dissociation we used exposure to a low concentration of the protease dispase (0.7 mg/ml for ~30 min). To enhance the survival of pluripotent stem cells and facilitate the transition into suspension, the ROCK inhibitor Y-27632 was added for the first 24 hours (day 0). Suspended colonies were subsequently transferred into low-attachment plastic plates in a Knock-Out Serum™ (Invitrogen) based media without fibroblast growth factor 2 (FGF2). Within a few hours following enzymatic detachment, the floating hiPSC colonies folded into spherical structures.

To achieve rapid and efficient neural induction, both the BMP and TGF-β signaling pathways were inhibited for 5 days with two small molecules: dorsomorphin (also known as compound C) and SB-431542. On the sixth day in suspension, the floating spheroids were moved to a serum-free B-27™ (Invitrogen) neural media containing FGF2 and epidermal growth factor (EGF) for 19 days, to support the expansion of neural progenitors. We used daily media change in the first 10 days, and every other day for the subsequent 9 days. This simple patterning approach generates cells with a dorsal forebrain fate, with over 85% of cells expressing PAX6 and more than 80% of these progenitors expressing FOXG1 by 18 days in vitro (FIG. 1). To promote differentiation of the neural progenitors into neurons, FGF2 and EGF were replaced with brain-derived neurotrophic factor (BDNF) and neurotrophic factor 3 (NT3) starting at day 25. From day 43 onwards only neural media without growth factors was used for media changes every 4 days, making long-term maintenance undemanding and relatively inexpensive.

Figure 1C:
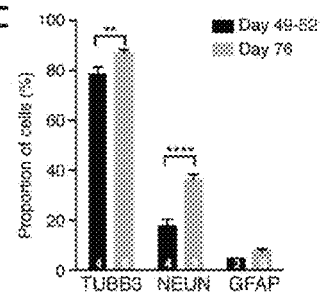

After ~7 weeks of differentiation in vitro, 78.8%±2.5 (mean±s.e.m.) of the cells expressed the neuronal marker 133-tubulin (TUBB3) (FIG. 1c). We also observed a small population of cells (7.6%±1.02, mean±s.e.m., at day 76)

expressing the astrocyte and radial glial marker GFAP. Remarkably, at this stage, 36.2%±3.6 (mean±s.e.m.) of neurons expressed the mature neuronal marker NEUN, which is present in the human forebrain only after 20 weeks of gestation.

Figure 1D:
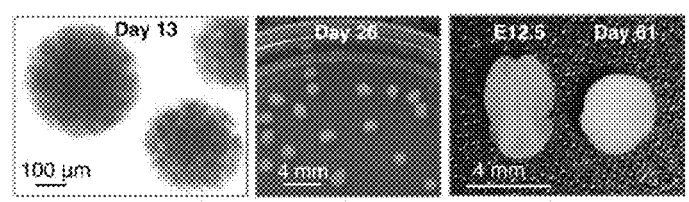

The floating neural spheroids grew in size to more than 300 μm in diameter by two weeks of culture in suspension and reached up to 4 mm in diameter by 2.5 months (4.2±_0.3 mm, mean±s.e.m., n=16 from 4 differentiated hiPSC lines) (FIG. 1d).

Figure 1E:
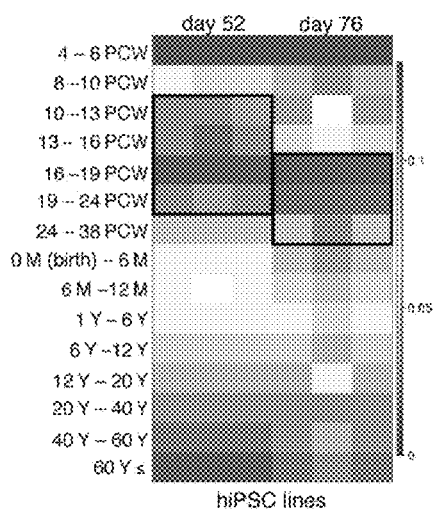
Figure 7:
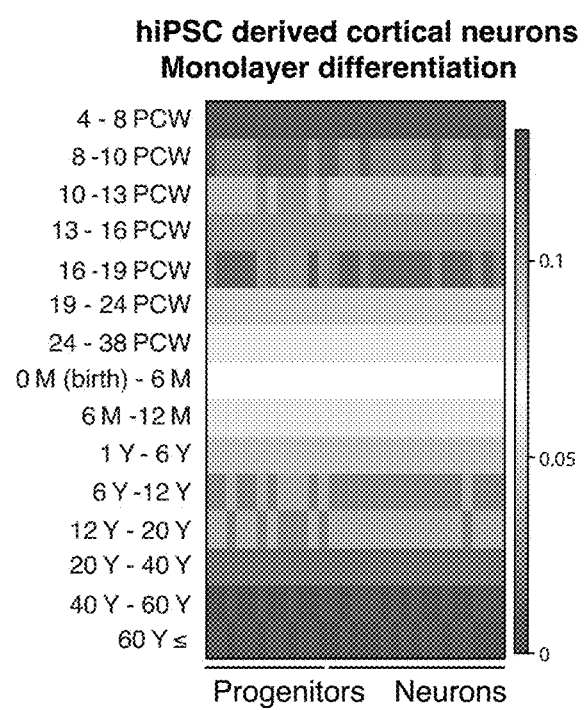
FIG. 7. Transcriptional analyses and mapping of neuronal cultures derived from hiPSC using a monolayer approach The machine learning algorithm CoNTExT, which matches transcriptomes to human brain development, was used to predict the in vivo temporal identity of neural progenitors and neurons differentiated from hiPSC using a monolayer approach. In contrast to the hCSs in FIG. 1e that reach up to stage 6, these cultures map to earlier stages of brain development.
Figure 8A:
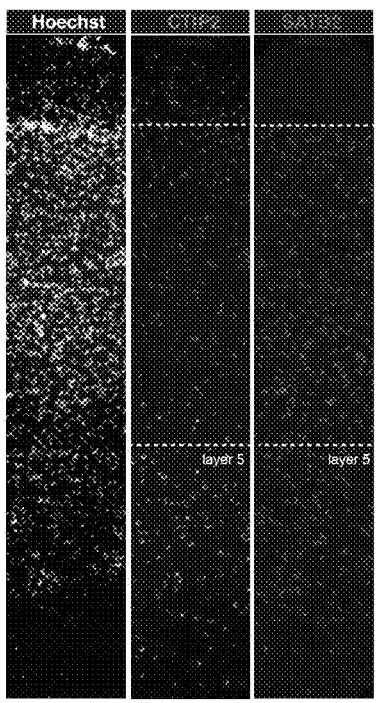
FIG. 8A-8D. Validation of layer specific antibodies in the human fetal cortex at GW36.
Figure 8B:
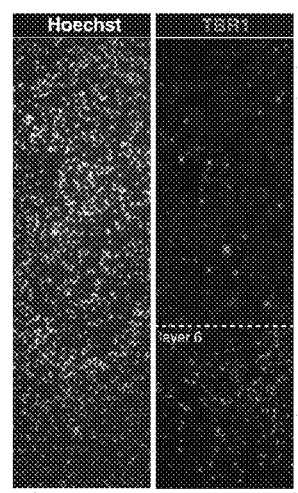
Figure 8C:
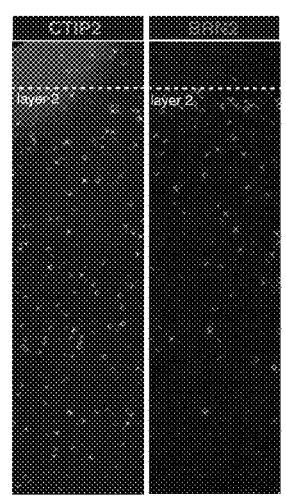
Figure 8D:
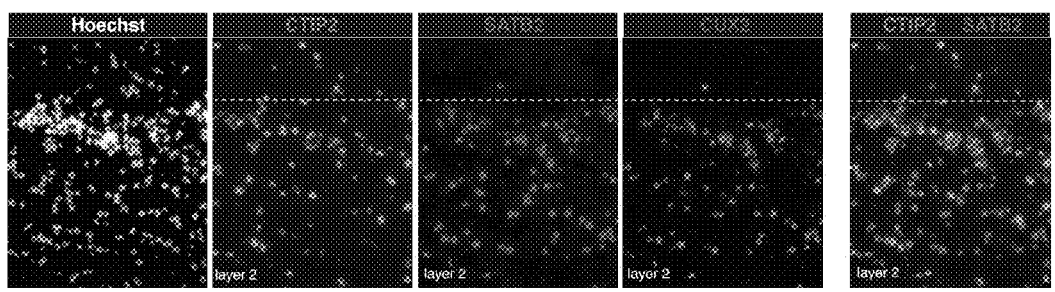

Because single markers provide an incomplete measure of cellular identity, we used genome-wide transcriptional profiling to better assess the developmental maturity and the regional identity of hCS at two distinct time points. We compared the in vitro transcriptional profiles to the developing human fetal brain using a machine learning algorithm (CoNTExT) trained on 1340 primary tissue samples collected from 57 developing and adult post-mortem brains, and validated on several hundred additional samples. There was a strong and highly significant overlap between the hCS and cortical developmental stages up to late mid-fetal periods (19-24 post-conception, PCW) (FIG. 1e; hiPSC derived from 3 individuals). This is in contrast to monolayer methods as well as other 3D approaches for neural differentiation of hiPSCs that yield neurons mapping onto earlier fetal stages (FIG. 7).

To gain further insights into these findings, we looked for the genes changing in the same direction in hCSs and human fetal cortex between stages 1 & 2 (4-10 PCW) and stage 6 (19-24 PCW), but not in hiPSC-derived neural cultures differentiated in monolayer (Table 1). Interestingly, up-regulated genes were enriched for synaptic transmission genes (GO enrichment, P=0.009), while the down-regulated genes were enriched for cell cycle (P=0.02) and cell division (P=0.001) genes.

Figure 1F:
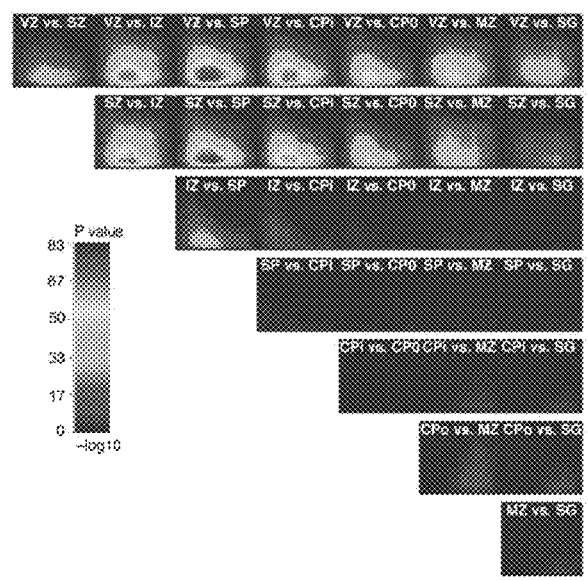

We next used Transition Mapping, which is based on a series of Rank-Rank Hypergeometric Overlap (RRHO) tests, to assess the similarity of the transcription transitions between in vitro development of the hCS and two time points in the developing human brain. For this analysis we employed the transcriptional spatiotemporal atlas of the human brain and the laminar expression data dissected via laser capture microdissection from fetal human brain. We found that the transition between day 52 and day 76 of in vitro development had the strongest overlap (−max-log 10(P value) >83) to the ventricular zone (VZ)/subventricular zone (SVZ) and to the intermediate zone (IZ)/subplate (SP)/inner cortical plate (CPi), respectively (FIG. 1f; n=3 hiPSC lines per time point).

To examine the cytoarchitecture of the hCS, we studied 10 μm cyrosections with immunocytochemistry. At day 52, we observed proliferative zones containing PAX6 expressing progenitors (FIG. 2a). Similar to in vivo cortical development, a VZ-like structure inside the hCS is organized around a lumen delimited by N-Cadherin (NCAD) expressing cells (FIG. 2b). Furthermore, the VZ is surrounded by an intermediate region rich in TBR2-expressing progenitors cells resembling a subventricular zone (SVZ) (FIG. 2b). The PAX6-expressing cells in the VZ-like zone also contain GFAP+ extensions directed orthogonally to the luminal surface, strongly resembling radial glia (FIG. 2c). When plated in monolayer, these cells either have bipolar or monopolar features (FIG. 2d, e).

Both PAX6+ and TBR2+ neural progenitors were actively proliferating as assessed by the expression of the radial glia-specific mitotic marker phospho-vimentin (p-VIM) and the later G2/M phase marker phospho-histone-3 (PH3) (FIG. 2f, g). Similar to in vivo cortical development, most of these mitoses were localized close to the luminal side of the proliferative zone rather than being dispersed across the VZ-like region. Moreover, live imaging of radial glia fluorescently labeled with a cell-specific reporter (GFAP::EGFP) revealed a characteristic division mode reminiscent of the interkinetic nuclear migration, in which the nucleus moves towards the lumen of the VZ-like region prior to cytokinesis (FIG. 2h).

To characterize the neuronal cell subtypes present in the hCS and to study the timing of their generation, we validated a panel of antibodies in the human fetal cortex (36 PCW) as probes for deep and superficial layer cortical identify (FIG. 8). On the surface of the hCS we observed a layer of horizontal cells expressing reelin (RELN), suggestive of a marginal zone (MZ) (FIG. 2i). We then used this set of validated markers to quantify the relative proportion of cells on cryosections at three separate time points (two way ANOVA, F(2, 48)=32.96, P<0.0001 for timepoint; n=3-13 spheres per condition from 4 iPSC lines derived from 4 individuals) from 4 iPSC lines derived from 4 individuals) (FIG. 2j). The T-box homebox protein TBR1, localized in SP and CP and later in layers V-VI, reached a peak of expression (40.7%±0.3 of all cells, mean±s.e.m.) at day 76 (equivalent of SP and CPi) and significantly decreased relative to other markers over time. CTIP2, a transcription factor that is both necessary and sufficient for specifying subcortical projection neurons, was highly expressed early in the hCS, and decreased over time after the in vitro stage equivalent to the early mid-fetal period, as previously shown in the human neocortex.

In contrast, superficial layer cortical markers increased up to 7-fold from day 52 to day 137 in vitro (SATB2 from day 46 to day 137, Tukey's multiple comparison, P<0.0001). The transcription factor BRN2 (or POU3F2), which is also expressed in late cortical progenitors and migrating neurons, reached a peak of expression earlier than the DNA-binding protein SATB2, which defines cortico-cortical projecting neurons. Moreover, the relative proportion of superficial layer neurons was also confirmed by the expression of the homeodomain family proteins CUX1 and CUX2, whose expression is mostly localized to layers II-IV. Importantly, we found that the generation of these neurons is highly reproducible between hiPSC lines, and within and across differentiations of the same hiPSC line (FIG. 9).

To provide independent validation of the quantification of neural populations from cryosections, we turned to flow cytometry. We dissociated hCS into single cell suspensions and used antibodies to quantify the exact proportion of distinct neuronal and glial populations (FIG. 10). The flow cytometry data correlated closely to the counts from the cryosectioned specimens. Considering the early presence of organized proliferative zones and the sequential generation of layer-specific cortical neurons, we next explored the internal laminar cytoarchitecure of the hCS. We noticed that layer-specific cortical neurons were organized in concentric circles around a VZ-like zone (FIG. 2k, l). Deep layer neurons expressing TBR1 and CTIP2 moved immediately outside of the proliferative zone, while at in vitro day 137 superficial layer cortical neurons expressing SATB2 and BRN2 had migrated farther away, forming the outside layer of the hCS. We also examined whether the co-localization of some of these cortical markers was consistent with in vivo studies. Indeed, flow cytometry experiments indicated that the mutually exclusive CTIP2 and SATB2 proteins, which regulate alternate cortico-fugal and cortico-cortical cellular identity programs, are coexpressed by fewer than 3% of the cells (FIG. 2m). In contrast, as expected from a laminated cortical anlage, the cortical layer markers TBR1 and CTIP2, which are expressed by subtypes of cortico-fugal neurons in deep layers and a small proportion of neurons in layer II, are co-localized in ~30% of the cells at day 76 in vitro (FIG. 2n).

In the developing cortex, deep and superficial layers are generated sequentially in an inside-outside manner. We explored whether the order of in vitro generation of various cortical layer neurons reflected the in vivo developmental program by labeling cells with 5-ethynil uridine (EdU) for 48 hours at day 55 (FIG. 2o, p). In cryosections of hCS fixed 3 weeks later, we observed that while the vast majority of SATB2-expressing cells co-localized with EdU, almost none of the TBR1-expressing cells contained EdU labeling. This indicates that most of the superficial layer neurons are formed after 8 weeks of differentiation in vitro. This process continues for at least another 7 weeks, until the proportion of superficial and deep layer neuron is approximately equal (FIG. 2j). Together, these experiments demonstrate the sequential generation of dorsal forebrain proliferative zones and laminated human cortex in 3D cultures from hiPSCs.

Identification and verification of astrogenesis in hCS. It is well established that neurons and astrocytes share a common neuroepithelial origin and are born throughout embryogenesis in a temporally defined manner. In the mammalian system, neural stem cells initially maintain an exclusively neurogenic fate. Once the bulk of neurogenesis has occurred, these neural progenitors become the primary source of astrocytes. Building on these developmental principles, we hypothesized that due to the longer exposure to FGF2 and EGF in our protocol, progenitors in the proliferative zones would ultimately undergo the neurogenesis-to-gliogenesis switch. At early time points, dividing $GFAP^+$ cells that co-expressed PAX6 or TBR2 were localized only inside the VZ/SVZ-like zones (FIG. 2c-f). However, after ~7 weeks of differentiation in vitro, we observed astrocytes with thin GFAP+ processes intermingled with NEUN+ cells (FIG. 3a).

To investigate the ultrastructure of the neuro-glial interactions in hCS, we utilized array tomography (AT), a high-resolution imaging technique based on the use of ribbons of ultrathin serial sections (70 nm). These ribbons can be probed with multiple rounds of immunofluorescent labeling, imaging and antibody elution allowing over 20 different proteins to be localized within a single large tissue volume. We observed numerous GFAP+ branches traversing the dense neuropil and intricately intertwined with neuronal MAP2+ processes (FIG. 3b).

We then verified whether astrogenesis in the hCS increases with time in vitro as expected from studies of fetal brain development. We dissociated hCS at multiple time points and quantified the number of GFAP+ cells (FIG. 3c, d). Furthermore, we confirmed these percentages using flow cytometry (FIG. 10). As expected, we observed few GFAP+ cells over the first 35 days of differentiation (2.7%±0.7). The number increased steadily and GFAP+ cells were distributed throughout the parenchyma of the hCS, reaching ~8% by day 76 and almost 20% by 181 days in vitro (FIG. 3c, d; ANOVA, $F(8, 19)=66.75$, $P<0.0001$).

Figure 11:
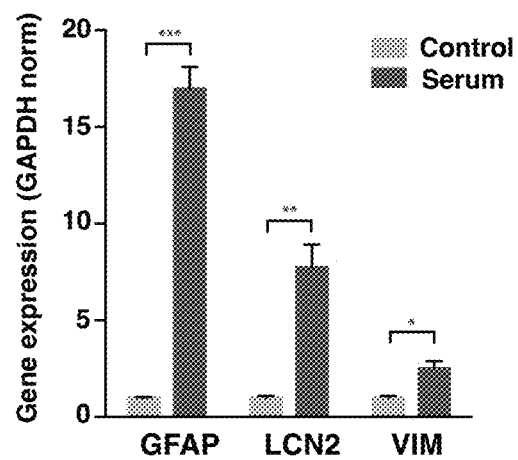
FIG. 11. Expression of activation markers in hCS following serum exposure Plated hCSs were cultured in Neurobasal/B27 media with our without 20% serum (FBS). After 5 days, cells were harvested and the expression of genes associated with astrocyte activation (GFAP, VIM, LCN2) was measured by qPCR (t-tests with multiple comparison corrections using the Holm-Sidak method; n=3 for each gene, *, P<0.05; , P<0.01; *P<0.001).

We also closely examined the morphology of GFAP+ cells following dissociation. When maintained in monolayer in defined serum-free culture conditions 51, astrocytes extended abundant thin projections (FIG. 3e). To investigate whether these cells could respond to reactive cues in vitro, we added serum to the culture media, which is a known activator of reactive astrogliosis. Within several days, the cells adopted a reactive phenotype with polygonal morphologies and significantly upregulated genes associated with activation of astrocytes in vivo, such as GFAP, VIM or LCN2 (FIG. 11). Finally, we used electron microscopy to confirm that the thin GFAP+ processes dispersed throughout the hCS contained numerous glycogen granules (FIG. 3f), which are predominantly localized in astrocytes in the mammalian brain. These experiments demonstrate that the hCS give rise to astrocytes in a temporally defined manner that recapitulates fetal cortical development, and most importantly, that these astrocytes populate their parenchyma in a resting, nonactivated state.

Figure 4A:
FIG. 4A-4E. Functional characterization of cortical neurons in hCS.
Figure 4B:
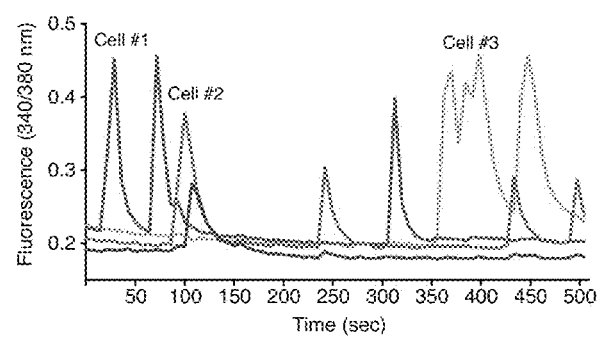
Figure 4C:
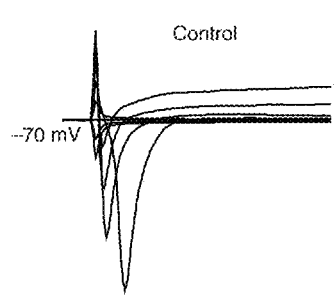
Figure 4D:
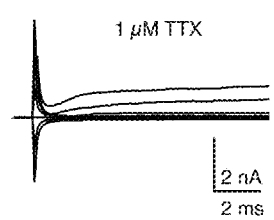
Figure 4E:
Figure 6:
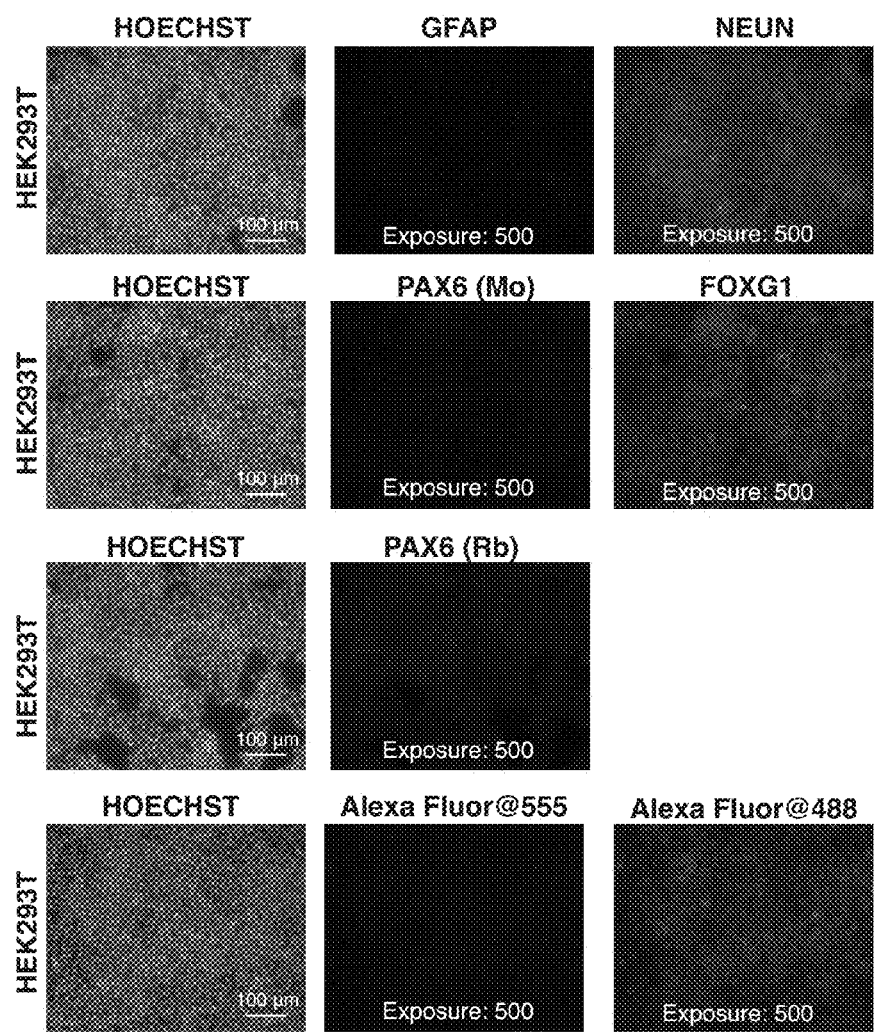
FIG. 6. Antibody specificity. Panel showing the specificity of the antibodies against NEUN, GFAP, FOXG1, PAX6 (Rb), PAX6 (Mo) in negative cells (HEK293T). The last row shows background imunostaining for secondary-only conditions. All images were collected at a 500 exposure.

Functional maturation and synaptogenesis in hCS. Next we tested the ability of the cells in hCS to differentiate into electrically active mature neurons. We first imaged neurons plated in monolayer from ~130 day-old hCS using the ratiometric calcium dye Fura-2. In contrast to neuronal cultures derived in monolayer from hiPSC, neurons in the hCS displayed abundant spontaneous calcium spikes (FIG. 4a, b) indicating increased functional maturity. We also directly loaded hCS with the fluorescent calcium indicator Fluo-4, acutely sectioned the spheroid and immediately imaged the cells with a confocal microscope. Again, we observed spontaneous calcium spikes. We then used patch clamping to record from human cortical neurons. We found that all recorded neurons (n=28) produced a transient inward current after depolarization beyond −30 mV (FIG. 4b). The current was blocked by tetrodotoxin (TTX) (FIG. 4c), indicating that it was mediated by voltage-gated Na+ channels. This inward voltage-gated Na+ current was followed by activation of a more sustained K+ current. Importantly, depolarizing current injection revealed that all of the recorded neurons could reliably produce action potentials (n=9) (FIG. 4d, e).

Considering the functional maturity of the cortical neurons and the presence of astrocytes, we decided to investigate synaptogenesis within the hCS. We first used AT, a high-resolution imaging technique that allows for the light-level visualization of individual synapses within the dense neuropil of the brain. Antibodies against multiple pre- and post-synaptic proteins were employed to identify individual synapses with a high degree of confidence. We found that the presynaptic protein synapsin-1 (SYN-1) and postsynaptic protein PSD-95 were expressed throughout the interior of the hCS in both large and small puncta (FIG. 5a). Larger SYN-1 puncta were often found adjacent to PSD-95 puncta indicating the presence of a synapse.

To examine these larger puncta in further detail, we constructed 'synaptograms' consisting of a series of high-resolution sections through a single synapse, where we could probe for potential co-localization of at least three independent synaptic markers. In many cases, we observed the co-localization of the presynaptic proteins SYN-1 and the glutamate transporter VGLUT1 in close apposition to postsynaptic protein PSD-95 indicating the presence of a glutamatergic synapse (FIG. 5b). Smaller SYN-1 and VGLUT-1 puncta are likely to be either nascent synapses or transport vesicles. In some cases, the NMDA receptor subunit NR2B was co-localized with the PSD-95 as well. In addition, synaptic size was consistent with what was reported in the neuropil of the adult human cerebral cortex. Thus, the expression patterns of these proteins and size suggest the presence of human synapses in hCS.

We continued the characterization of these synapses at the electrophysiological level and found that the majority (88.8%) of neurons exhibited spontaneous synaptic activity (n=27 neurons), This activity was completely abolished by the application of the AMPA-receptor antagonist NBQX (25 pM) and the NMDA-receptor antagonist D-AP5 (50 pM) (frequency NBQX+D-AP5 versus artificial cerebrospinal fluid (ACSF), paired t-test, n=11 cells, P=0.001) suggesting that synaptic currents are solely due to the activation of glutamate receptors (FIG. 5c; FIG. 12a). Further characterization of the synaptic activity revealed that TTX (1 μM) significantly reduced the amplitude (TTX versus ACSF, unpaired ttest, n=10 cells, P<0.0001) and frequency of EPSCs (Wilcoxon signed-rank test, n=10, P=0.002) by approximately 50% (FIG. 12, FIG. 5d, e), suggesting that half of the events observed were evoked by action-potential dependent vesicle release and the remainder were due to spontaneous vesicle release.

To characterize the neural network in an increasingly intact system, we established slice physiology methods in hCS. We cut hCS into 250 μm sections and performed acute whole cell recordings (FIG. 5f). We found that 80% of neurons (n=15) fire action potentials in response to depolarizing current steps from a holding potential of −65 mV (FIG. 13a). The large majority of neurons (86%, n=15) exhibited spontaneous synaptic activity (FIG. 5g; FIG. 13b) that was significantly reduced by kynurenic acid, a glutamate receptor blocker (FIG. 5g; FIG. 10c, t-test, n=6 cells; P=0.0008). Following patch-clamp recordings, neurons were labeled with biocytin to reveal their morphology (FIG. 5h). Importantly, in response to extracellular electrical stimulation, we observed large amplitude EPSPs (>20 pA) demonstrating that cortical neurons in hCS participate in network activity (FIG. 5i; FIG. 13d, e). In order to determine if these synaptic responses are capable of driving spike firing in hCS neurons, current clamp recordings were performed in which no holding current was applied while administering periodic electrical stimulation. Single spikes as well as burst events were observed following stimulation (FIG. 5j, FIG. 13f). Spontaneous spiking events were also observed in the absence of stimulation. These results demonstrate that an active network exists within hCSs capable of producing complex synaptic events associated with postsynaptic neuronal spike firing.

Taken together, these data demonstrate that neurons differentiated from hiPSC using this 3D approach display spontaneous calcium rises, reproducibly express voltage-gated Na+ and K+ currents, fire action potentials, form synapses and exhibit robust spontaneous and stimulus-triggered synaptic activity. This is consistent with properties of mature cortical neurons in vivo.

To date, several approaches have been developed for differentiating mouse and human pluripotent stem cells (hES and hiPSC) into cortical neurons. Some of these methods achieve neural induction in high-density monolayer cultures or by embedding clusters of hiPSCs in gelatinous protein mixtures (e.g., Matrigel) and later culturing in a spinning bioreactor. Alternatively, other approaches use embryoid bodies (EBs) derived from hiPSCs that are either plated on coated surfaces to generate neural progenitors organized in rosettes or maintained in suspension initially in serum-free conditions and later in serum and Matrigel (i.e, SFEBq). Most of these protocols are laborious, yield neurons that often seem to be stalled at an immature stage of differentiation, do not generate astrocytes and do not give rise to functional neural network that can be perturbed and probed in cytoarchitecturally intact preparations.

Here we describe an effective approach for in vitro neural differentiation of human pluripotent stem cells, which shows several advantages over existing techniques. This protocol, involving detachment of intact hiPSC from their feeder layer, is simple and robust, and does not involve (re)-plating, embedding into extracellular matrices or culture in bioreactors. While some groups used patterning molecules, such as retinoids or inhibitors of the sonic hedgehog pathways, we found that early double SMAD inhibition and a simple expansion in FGF2 and EGF are sufficient to generate mature cortical neurons. Both immunocytochemistry and electrophysiology indicate that these neurons are excitatory, as expected. Due to the fact that the hCS are maintained in floating conditions on low attachment plates with bi-weekly media changes, we were able to easily maintain stable cultures for up to 9 months in vitro.

Moreover, the protocol is reproducible between hiPSC lines, within and between differentiation experiments. For instance, the average standard deviation across multiple hCS for several layer-specific cortical markers at 137 days of differentiation is only 3.1%. The ability to evaluate the proportion of various cell types using flow cytometry indicates that this differentiation platform could be reliably used for studying human disease and for detecting subtle defects in neuronal specification.

Using immunocytochemistry and flow cytometry with antibodies validated in human fetal cortical tissue as well as EdU labeling, we demonstrated the sequential generation of deep and superficial layer cortical neurons. In comparison to existing 3D neural differentiation approaches, we obtained equal proportions of superficial and deep layer neurons. Interestingly, the neurons expressing layer specific markers are organized concentrically with superficial layer cells arranged on the outside. The advanced in vitro corticogenesis and the cytoarchitecture of the hCS will provide new opportunities to address fundamental questions related to the expansion of superficial cortical layers in primates as well as to identify defects associated with neurodevelopmental disorders.

Unlike previous monolayer or 3D protocols, we present a system in which human astrocytes and neurons are generated together from an identical genetic background.

Despite previous dogma, astrocytes are not mere passive bystanders of nervous system development. They powerfully control synapse formation and function, and are critical for proper neural development. In our hCS, we observed a steady increase in astrocyte number throughout in vitro differentiation, recapitulating the gradual neurogenic to gliogenic transition of neural stem cells during fetal brain development. The astrocytes are generated solely in response to the intrinsic temporal dynamics of forebrain neural progenitor cells and are not dependent upon the application of exogenous cues. In contrast to existing protocols for generating human astrocytes from hiPSCs or by direct conversion, the astrocytes dispersed throughout the hCS develop spontaneously without the need for CNTF, LIF, or serum, which are known activators of reactive astrocyte phenotypes. In fact, we observe that in vitro serum administration quickly results in stereotyped morphologic transformations that are typical of reactive phenotypes, supporting the idea that astrocytes residing in these 3D cultures are quiescent.

Neurons in the hCS are more transcriptionally and electrophysiologically mature than neurons generated through conventional methods. Gene expression maps the age of 3D cultures to the human fetal cortex in the late second trimester, while previous protocols using transcriptional analyses yielded cultures similar to the early first trimester developing brain. By 11 weeks in culture, one third of the neurons in the hCS express the mature marker NEUN, which is only expressed after 22 PCW in the fetal human cortex 29. Importantly, all recorded neurons fired action potentials in contrast to ~50% of neurons derived in monolayer, and displayed spontaneous calcium spiking activity. In contrast, others have reported spontaneous electrical activity in hiPSC-derived neurons only after 3 months in vitro and following co-culture with astrocytes.

The hCS display robust synaptogenesis. The generation and close spatial integration of astrocytes inside the spheroids contribute to the robust formation of functionally mature synapses. AT and EM data demonstrate that astrocyte processes are closely intertwined with the neuropil in the 3D structure. This dense neuro-glial integration may enhance astrocyte-neuron contact and mediate synaptogenic mechanisms that ultimately produce robust synaptic responses. Synaptogenic properties of astrocytes, usually isolated from rodents or human fetal tissue, are commonly exploited in hiPSC neural differentiation protocols to force neuronal maturation and for studying disease 73. Co-culturing, whether with rodent or human astrocytes, is laborious and could often mask cell nonautonomous phenotypes in neurons.

Importantly, hCS can be readily adapted to established slice physiology techniques, which have been extensively used to study cortical circuits in animal brain slices. Excitatory neurons within these acutely prepared slices are capable of repetitive action potential generation, and producing spontaneous, glutamate-dependent, synaptic responses. Importantly, these neurons participate in a neural network involving complex synaptic events that result in postsynaptic neuronal spike firing. This type of intact preparation represents a powerful approach for studying human neurons embedded in neural networks during corticogenesis and under disease states.

Because these hCS are cultured in a regular serum-free neurobasal media without embedding and multiple plating steps, they represent a versatile platform for patterning and specification of various neuronal and glial cell types, as well as for designing large scale drug screening in vitro. The approach presented here for generating cortical progenitors, neurons and astrocytes starting from pluripotent stem cells represents a powerful 3D platform for studying specific aspects of human brain development in vitro, including specification of superficial layer neurons, lamination and astrogenesis. Moreover, with the advent of reprogramming technologies and the ability to derive hiPSCs from unique patient populations, it provides a convenient, and physiologically relevant means for studying neuropsychiatric disorders, including synaptopathies and epilepsies.

Experimental Procedures

Culture of hiPSCs.

hiPSCs were cultured on irradiated DR4 mouse embryonic fibroblast feeders in the following cell culture media: DMEM/F12 (1:1) (Invitrogen) containing 20% Knock-Out Serum™ (Invitrogen), 1 mM non-essential amino acids (Invitrogen, 1:100), GlutaMax™ (Invitrogen, 1:100), 0.1 nM β-mercaptoethanol (Sigma-Aldrich), 100 U/ml penicillin and 100 pg/ml streptomycin (Invitrogen) and 10-15 ng/ml FGF2 (R&D Systems). The lines/clones of hiPSC used in this study were validated using standardized methods as previously shown. A total of 7 iPSC lines derived from 5 subjects were used for experiments. Approval for this study was obtained from the Stanford IRB Panel and informed consent was obtained from all subjects.

Generation of hCS from hiPSC.

For dissociating intact colonies of pluripotent stem cells from the layer of DR4 feeders, hiPSC were exposed to a low concentration of dispase (Invitrogen: 17105-041; 0.7 mg/ml) for ~30 min. Suspended colonies were subsequently transferred into ultra-low attachment 100 mm plastic plates (Corning) in hiPSC media without FGF2. For the first 24 hours (day 0), the media was supplemented with the ROCK inhibitor Y-27632 (EMD Chemicals). For neural induction, dorsomorphin (also known as compound C; Sigma 10 pM) and SB-431542 (Tocris, 10 pM) were added to the media for the first 5 days. On the sixth day in suspension, the floating spheroids were moved to neural media (NM) containing Neurobasal (Invitrogen: 10888), B-27 without vitamin A (Invitrogen: 12587), GlutaMax™ (Invitrogen, 1:100), 100 U/ml penicillin and 100 μl streptomycin (Invitrogen). The NM was supplemented with 20 ng/ml FGF2 (R&D Systems) and 20 ng/ml EGF (R&D Systems) for 19 days with daily media change in the first 10 days, and every other day for the subsequent 9 days. To promote differentiation of the neural progenitors into neurons, FGF2 and EGF were replaced with 20 ng/ml BDNF (Peprotech) and 20 ng/ml NT3 (Peprotech) starting at day 25, while from day 43 onwards only NM without growth factors was used for media changes every 4 days.

Cryopreserving.

The hCS were fixed in 4% paraformaldehyde (PFA) overnight. They were then washed in PBS, transferred in solution of 30% sucrose and kept at 4° C. for 48-72 hours. Subsequently, they were transferred into embedding medium (Tissue-Tek OCT Compound 4583, Sakura Finetek), snap-frozen on dry ice and stored at −80° C. Using a cryostat, 10 μm thick sections of the spheroids were obtained.

Immunohistochemistry.

Cryosections were washed with PBS to remove excess OCT and blocked in 10% normal goat serum (NGS), 0.1% bovine serum albumin (BSA), 0.3% Triton X-100 diluted in PBS for 1 hour at room temperature. The sections were then incubated overnight at 4° C. with primary antibodies diluted in solution containing 2% NGS and 0.1% Triton X-100. PBS was used to wash the primary antibodies and the cryosections were incubated with secondary antibodies containing 2% NGS and 0.1% Triton X-100 for 1 hour. The following primary antibodies were used for immunocytochemistry: PAX6 (rabbit, 1:300; Covance: PRB-278P), PAX6 (mouse, 1:300; DSHB), p-Vimentin (mouse, 1:2000; Abcam: ab22651), NCAD (mouse, 1:50; Santa Cruz: 8424), FOXG1 (rabbit, 1:500; NCFAB), NEUN (mouse, 1:500, Millipore: MAB377), MAP2 (guinea pig, 1:1000; Synaptic Systems: 188004), GFAP (rabbit; 1:500; DAKO: Z0334), SATB2 (mouse, 1:50; Abcam: AB51502), CTIP2 (rat, 1:300; Abcam: AB18465), TBR1 (rabbit, 1:200; Abcam: AB31940), TBR2 (rabbit, 1:300; Abcam: AB23345), BRN2 (mouse, 1:50; Millipore: MABD51), RELN (mouse, 1:200; MBL: D223-3). AlexaFluor™ Dyes (LifeTechnologies) were used at 1:1000 dilution for amplifying the signal. Nuclei were visualized with Hoechst 33258 (LifeTechnologies, 1:10,000). Cryosections were mounted for microscopy on glass coverslips, using Aquamount (ThermoScientific) and imaged on a Zeiss M1 Axioscope with a 10×, 20×, 40× or 63× objective. All cells expressing a particular marker were counted on sections and normalized to the total number of cells.

Gene Expression.

RNA was isolated using the miRNeasy Micro Kit (Qiagen) and RNA integrity was assessed by obtaining a RIN score on the Agilent 2100 Bioanalyzer. All of the RNA samples had a RIN >8. Total RNAs were amplified, labeled and hybridized on HumanHT-12 v4 Expression BeadChips (Illumine) according to the manufacturer's protocol. Microarray data was analyzed with custom R scripts calling Bioconductor (http://www.bioconductor.org/) packages. Briefly, outlier arrays were detected based on low inter-sample correlations. Raw expression data was log 2 transformed, and quantile normalized. Probes were considered robustly expressed if the detection P value was <0.05 for at least half of the samples in the data set. Regional and temporal identify of the cells regarding to brain development was assessed using CoNTExt.

Flow Cytometry.

Cells were stained with a viability dye (Live/dead Blue, Invitrogen, 1:1000 in PBS) for 10 minutes on ice in the dark. A volume of 100 µl of PBS was subsequently added to the cell suspension and the pellet was spanned down at 1800 rpm for 5 minutes. The supernatant was decanted and cell pellets were subjected to intracellular staining. For intracellular staining, cells were permeabilized with a transcription factor staining buffer set (Ebiosciences). Briefly, cell pellets were resuspended in 200 µl permeabilization buffer and incubated on ice in the dark for 20 minutes. A 200 µl perm-wash buffer was subsequently added to cell suspension and the samples were centrifuged at 1800 rpm at 4° C. for 5 minutes.

The supernatant was decanted and samples were stained with antibodies in 100 µl permwash buffer on ice in the dark for 20 minutes. Finally, 200 µl of PBS was added to the cell suspensions and the samples were centrifuged at 1800 rpm at 4° C. for 5 minutes. Cell suspensions were stored in 1% PFA in PBS at 4° C. until analysis. The following antibodies were used: CTIP2 (rat, 1:100; Abcam: AB18465), TBR1 (rabbit, 1:100; Abcam: AB31940), BRN2 (mouse, 1:50; Millipore: MABD51), SATB2 (rabbit, 1:50; Epitomics, 2819-1), CUX1 (mouse, 1:100; Abnova: H00001523-M01). The anti-CUX2 antibody was generated in rat, tested in human fetal cortex and used at dilution of 1:100. The following secondaries were used: anti rat Alexa 647, anti mouse PE, anti rabbit Alexa 488 (dilution 1:5000). The LSRII system (BD Biosciences) was used for data acquisition, while data analysis was performed with FlowJo (Treestar). Cellular events were gated for singlets (FSC-A versus FSC-H) to exclude potential cell clumps. Dead cells were then excluded from singlet population by elimination of cells that stained positive for Live/dead Blue. Negative threshold gates were defined with control samples (secondary antibodies alone). Examples FACS plots are shown in FIG. 7.

Live Imaging.

For visualizing radial glia, hCS were infected with a lentivirus expressing EGFP under the human GFAP promoter (Lenti-GFAP::EGFP). At day 52 of differentiation in vitro, hCS were sliced and VZ-like regions were imaged at 37° C. with a Leica SP8 confocal microscope for up to 3 hours.

Astrocyte Methods.

The hCS were enzymatically dissociated to make a suspension of single cells using a method used previously for dissociating brain tissue. Briefly, the tissue was incubated at 33° C. for 45 minutes in 20 ml of a papain solution containing Earle's balanced salts (EBSS, Sigma, E7510), D(+)-glucose (22.5 mM), NaHCO$_3$(26 mM), DNase (125 U/ml, Worthington, LS002007), papain (30 U/ml, Worthington LS03126), and L-cysteine (1 mM, Sigma, C7880). The papain solution was equilibrated with 5% CO2 and 95% O2 gas before and during treatment. The tissue was subsequently washed three times with an inhibitor buffer containing BSA (1.0 mg/ml, Sigma A-8806), and ovomucoid (also known as trypsin inhibitor, 1.0 mg/ml, Roche Diagnostics Corporation 109878) and then mechanically dissociated by gentle sequential trituration. Dissociated cells were layered on top of high concentration inhibitor solution with 5 mg/ml BSA and 5 mg/ml ovomucoid and centrifuged at 130 g for 5 minutes. The cell pellet was then resuspended in Dulbecco's phosphate-buffered saline (DPBS, Invitrogen, 14287) containing 0.02% BSA and 12.5 U/ml DNase and filtered through a 20 µm Nitex mesh (Sefar America Inc., Lab Pak 03-20/14) to remove undissociated cell clumps. Cell health was assessed by trypan blue exclusion. Only single cell suspensions with >85% viability were used for experiments.

Real Time Quantitative PCR (qPCR).

mRNA was isolated using the RNeasy Mini kit and RNase-Free DNase set (Qiagen). Template cDNA was prepared by reverse transcription using the SuperScript III First-Strand Synthesis SuperMix for qRT-PCR (Invitrogen). Gene expression was quantified using real time quantitative PCR in combination with gene specific primers and the SYBR GREEN system (Roche). The reactions were performed on an Eppendorf Realplex4 cycler (Eppendorf). All samples (n=3) were run in duplicate. Values were normalized to GAPDH expression. The following primers were used:

SEQ ID NO: 1, GADPH-fw:   (5'-GAACGGGAAGCTTGTCATCAA-3')

SEQ ID NO: 2, GADPH-rev:  (5'-ATCGCCCCACTTGATTTTGG-3')

SEQ ID NO: 3, GFAP-fw:    (5'-GAGAACCGGATCACCATTCC-3')

SEQ ID NO: 4, GFAPrev:    (5'-CCCAGTCTGGAGCAACCTAC-3')

SEQ ID NO: 5, LCN2-fw:    (5-GTTACCTCGTCCGAGTGGTG-3')

SEQ ID NO: 6, LCN2-rev:   (5'-TTGGTTCTCCCGTAGAGGGT-3')

SEQ ID NO: 7, VIM-fw:     (5'-CTCCGGGAGAAATTGCAGGA-3')

SEQ ID NO: 8, VIM-rev:    (5'-TTCAAGGTCAAGACGTGCCA-3')

Array Tomography.

Array tomography was carried out according to previously published protocols. Briefly, hCS were removed from their growth media and immediately fixed with 4% PFA, 2.5% sucrose in PBS. The tissue was embedded and sectioned into ribbons of 70 nm thick serial sections (30-50 sections/ribbon). Ribbons were stained in four consecutive sessions with the following antibodies: PSD-95 (rabbit, 1:200; Cell Signaling 34505), VGLUT1 (guinea pig, 1:5000; Millipore: AB5905); SYN-1 (rabbit, 1:500; Cell Signaling: 52975), MAP2 (guinea pig, 1:1000; Synaptic Systems: 188 004), GFAP (rabbit, 1:500; DAKO: Z0334), NR2B (mouse, 1:500; Neuromab: 75-101). The images were processed and registered for volume reconstruction using plugins from FIJI/ImageJ. The final volumes were rendered using AxioVision software (rel 4.7, Zeiss).

Calcium Imaging.

For calcium imaging in monolayer, dissociated hCS were loaded with 1 µM Fura-2 acetoxymethyl ester (Invitrogen) for 30 min at 37° C. in Neurobasal/B27 medium, washed with Tyrode's solution (5 mM KCl, 129 mM NaCl, 2 mM CaCl2, 1 mM MgCl2, 30 mM glucose and 25 mM HEPES, pH 7.4) and placed in a perfusion chamber on the stage of an inverted fluorescence microscope (TE2000U; Nikon). Imaging was performed at room temperature (23-25° C.) on an epifluorescence microscope equipped with an excitation filter wheel and an automated stage. The Openlab software (PerkinElmer) was used to collect and quantify time lapse excitation ratio images, and fluorescence images were analyzed with the IGOR Pro software (WaveMetrics). For calcium imaging in 3D cultures, intact hCS were loaded with 1 pM Fluo-4 acetoxymethyl ester (Invitrogen) for 30 min at 37° C. in Neurobasal with B27, washed and sliced in half. Live imaging was performed at the NMS (Stanford Neuroscience Microscopy Service) using a Zeiss LSM780 confocal microscope.

Monolayer Electrophysiology.

Whole-cell patch-clamp recordings from dissociated hCS were performed at room temperature in an isotonic saline solution (NaCl 125 mM, $NaHCO_3$ 25 mM, KCl 2.5 mM, NaH2PO4 1.25 mM, glucose 25 mM, MgCl2 1 mM, $CaCl_2$) 2 mM). Patch electrodes with resistances of 2.5-3.5 MΩ were pulled from thick-walled borosilicate glass capillaries and were filled with an internal solution containing (in mM) potassium gluconate 130, NaCl 4, EGTA 5, $CaCl_2$) 0.5, 10 HEPES, MgATP 4, Na2GTP 0.5 (pH 7.2 with KOH). Voltage-gated sodium and potassium currents were elicited with a series of voltage steps (from –110 to 10 mV, in 20 mV increments) from a holding potential of –70 mV. Spontaneous synaptic transmission was monitored in voltage-clamp from a holding potential of –70 mV. Action potentials evoked in response to current injection were recorded from the resting potential of the cell (applying 20 pA steps for 200 ms). Series resistance was monitored throughout the recording and was <20 MO. NBQX (25 pM, Tocris) and D-AP5 (50 pM, Tocris) were used to inhibit AMPA-receptor mediated and NMDA-receptor mediated excitatory synaptic responses, respectively. TTX (1 pM, Alomone) was used to block voltage-gated Na+ currents, and record mEPSCs. An Axopatch 200A amplifier (Molecular Devices) was used for voltage and current clamp, and electrode junction potentials were compensated. Data were sampled at 50 kHz and filtered at 1 kHz using pClamp 9.2, and offline analysis was performed using Clampfit 10.3 (Molecular Devices).

Slice Preparation.

hCS were removed from Neurobasal-B27 media, quickly fixed to a block of 4% agarose, and covered in ice-cold oxygenated (95% 02 and 5% CO2) ACSF containing 126 mM NaCl, 2.5 mM KCl, 1.25 mM NaH2PO4, 2 mM MgCl2, 2 mM $CaCl_2$), 26 mM $NaHCO_3$ and 10 mM glucose. 250 μm thick slices were cut using a Leica VT1200 vibrating microtome. After slicing, sections were moved to continuously oxygenated warm (~32° C.) ACSF. Slices were incubated in warm ACSF for at least one hour prior to recording.

Slice Electrophysiology.

Whole cell patch clamp recordings were made at 22-25° C. Slices were superfused at a rate of 3 ml/min. Patch-clamp recordings were made using a MultiClamp 700A amplifier with Clampex 10.3 software. 3-5 MO borosilicate glass recording electrodes were filled with internal solution containing 120 mM potassium gluconate, 11 mM KCl, 1 mM MgCl2, 1 mM CaCl2, 10 mM HEPES, 1 mM EGTA, pH adjusted to 7.4 with KOH (290 mOsm). To determine if EPSCs recorded in voltage clamp are glutamate dependent, the glutamate receptor blocker kynurenic acid (1 mM) was added to the bath solution following at minimum 5 min of baseline recording. Evoked responses were produced by extracellular monopolar tungsten electrode placed 100-300 μm from the whole cell recording. At the end of the recording biocytin was added to the internal solution, the slice was fixed and imunostained (Streptavidin, Alexa Fluor® 555 conjugate, LifeTechnologies) to visualize neuronal morphology. All electrophysiological experiments were performed in hCS between day 90 and 130 of in vitro differentiation.

Example 2

The methods as described in Example 1 have been adapted to generate hCS in fully defined, feeder-free and xeno-free cultures. A xeno-free culture contains no animal-derived component but may potentially contain human-derived components.

Pluripotent stem cells (hiPSC or hESC) are maintained with Essential 8 medium (Invitrogen) on human recombinant Vitronectin (Invitrogen)-treated vessels, and are passaged with 0.5 M EDTA. To improve differentiation across multiple hiPSC lines/clones, cells are treated 24 hours before starting the differentiation with 1% dimethyl sulfoxide (DMSO) (day –1) (Chetty et al, 2013 *Nature Methods*, 10(6), 553-6).

The single cell suspension of hiPSC or hESC is aggregated by centrifugation in microwells, and maintained in Essential 8 media with the ROCK inhibitor Y-27632 (Tocris) for 24 hours (day 0). Next day (day 1), spheroids are transferred to low attachment plates in Essential 6 medium (Invitrogen) with Dorsomorphin (Sigma, 5 pM), SB-431542 (Tocris, 10 pM) and XAV-939 (Tocris, 2.5 pM). No media change is performed the next day (day 2), but from day 3 to day 6, spheroids are maintained in Essential 6 medium (Invitrogen) with Dorsomorphin (Sigma, 5 pM), SB-431542 (Tocris, 10 pM) and XAV-939 (Tocris, 2.5 pM), with daily media changes. On day 7, spheroids are transferred to Neurobasal/B27 medium supplemented with the growth factors FG2 (20 ng/ml) and EGF (20 ng/ml), as described above for the protocol with hiPSC/hESC maintained on mouse embryonic fibroblasts (MEFs).

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

That which is claimed is:

1. A method for producing human cortical cells in vitro, the method comprising:
   (a) differentiating human pluripotent stem cells into a spheroid by culturing the human pluripotent stem cells in suspension culture for a period of from 2 to 10 days in medium comprising an inhibitor of bone morphogenetic protein (BMP) and an inhibitor of transforming growth factor β (TGFβ);
   (b) differentiating the spheroid of cells to neural progenitor spheroids by culturing in suspension culture for a period from 1 to 4 weeks in medium comprising fibroblast growth factor 2 (FGF2) and epidermal growth factor (EGF);
   (c) differentiating the neural progenitor spheroids into neuronal spheroids by culturing the neural progenitor spheroids in suspension culture for a period from 1 to 4 weeks in medium lacking FGF2 and EGF and comprising brain-derived neurotrophic factor (BDNF) and neurotrophin 3 (NT3);
   (d) maintaining the neuronal spheroid for a period of at least 1 to 12 months in a suspension culture in neural medium in the absence of growth factors
   to obtain a human cortical spheroid comprising human cerebral cortical neurons and astrocytes.

2. The method of claim 1, wherein the human cortical spheroid further comprises glial cells, neuro-epithelial cells, and oligodendrocytes.

3. The method of claim 1, wherein the astrocytes present in the cortical spheroid have a mature phenotype.

4. The method of claim 1, wherein the human pluripotent stem cells comprise at least one allele associated with a neurologic or psychiatric disorder.

5. The method of claim 1, wherein the human pluripotent stem cells are induced pluripotent stem cells.

6. The method of claim 1, wherein inhibitor of bone morphogenetic protein (BMP) and an inhibitor of transforming growth factor β (TGFβ) are dorsomorphin and SB-431542, respectively.

7. The method of claim 6, wherein the suspension culture is derived from human pluripotent stem cells maintained in feeder layer free conditions.

8. The method of claim 6, wherein the medium of step (a) further comprises an effective dose of an inhibitor of WNT signaling.

9. The method of claim 1, wherein the cortical spheroids comprise at least 10% astrocytes.

10. The method of claim 9, further comprising isolating astrocytes from a cortical spheroid by flow cytometry, magnetic immunoselection, or immunopanning.

11. The method of claim 1, wherein each of steps (a)-(d) are performed in substantially serum-free, xeno-free medium.

* * * * *